(12) United States Patent
Hinrichs et al.

(10) Patent No.: US 10,329,339 B2
(45) Date of Patent: *Jun. 25, 2019

(54) ANTI-HUMAN PAPILLOMAVIRUS 16 E6 T CELL RECEPTORS

(71) Applicant: The United States of America, as represented by the Secretary, Department of Health and Human Services, Washington, DC (US)

(72) Inventors: Christian S. Hinrichs, Bethesda, MD (US); Steven A. Rosenberg, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/786,966

(22) Filed: Oct. 18, 2017

(65) Prior Publication Data

US 2018/0094041 A1 Apr. 5, 2018

Related U.S. Application Data

(63) Continuation of application No. 14/905,108, filed as application No. PCT/US2014/046480 on Jul. 14, 2014, now Pat. No. 9,822,162.

(60) Provisional application No. 61/846,167, filed on Jul. 15, 2013.

(51) Int. Cl.
| | |
|---|---|
| *A61K 35/17* | (2015.01) |
| *C07K 14/725* | (2006.01) |
| *C07K 16/28* | (2006.01) |
| *G01N 33/566* | (2006.01) |
| *A61K 38/00* | (2006.01) |

(52) U.S. Cl.
CPC .......... *C07K 14/7051* (2013.01); *A61K 35/17* (2013.01); *C07K 16/2809* (2013.01); *G01N 33/566* (2013.01); *A61K 38/00* (2013.01); *C07K 2317/34* (2013.01); *C07K 2319/00* (2013.01); *G01N 2333/7051* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 5,087,616 | A | 2/1992 | Myers et al. |
| 5,225,539 | A | 7/1993 | Winter |
| 5,449,752 | A | 9/1995 | Fujii et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobobits et al. |
| 6,265,150 | B1 | 7/2001 | Terstappen et al. |
| 8,034,334 | B2 | 10/2011 | Dudley et al. |
| 8,383,099 | B2 | 2/2013 | Dudley et al. |
| 2002/0197266 | A1 | 12/2002 | Debinski |
| 2010/0189742 | A1 | 7/2010 | Van der Burg et al. |
| 2012/0244133 | A1 | 9/2012 | Rosenberg et al. |

FOREIGN PATENT DOCUMENTS

| | | |
|---|---|---|
| EP | 0239400 B1 | 8/1994 |
| GB | 2188638 A | 10/1987 |
| JP | H10-509948 A | 9/1998 |
| JP | 2013-505734 A | 2/2013 |
| WO | WO 96/15153 A1 | 5/1996 |
| WO | WO 2007/131092 A2 * | 11/2007 |
| WO | WO 2011/039508 A2 | 4/2011 |

OTHER PUBLICATIONS

Thomas et al. Int. J. Cancer, 122:2791-99 (2008).*
International Bureau, International Search Report in International Application No. PCT/US2014/046480, dated Oct. 28, 2014.
International Bureau, Written Opinion in International Application No. PCT/US2014/046480, dated Oct. 28, 2014.
Choi et al., "Synthesis and Assembly of a Cholera Toxin B Subunit-Rotavirus VP7 Fusion Protein in Transgenic Potato," *Mol. Biotechnol.*, 31: 193-202 (2005).
Dudley et al., "Generation of Tumor-Infiltrating Lymphocyte Cultures for Use in Adoptive Transfer Therapy for Melanoma Patients," *J. Immunother.*, 26: 332-42 (2003).
Evans et al., "Antigen Processing Defects in Cervical Carcinomas Limit the Presentation of a CTL Epitope from Human Papillomavirus 16 E6," *J. Immunol.*, 167: 5420-28 (2001).
Haskard et al., "The Production of Human Monoclonal Autoantibodies from Patients with Rheumatoid Arthritis by the EBV-Hybridoma Technique," *J. Immunol. Methods*, 74(2), 361-67 (1984).
Hudecz, "Synthesis of Peptide Bioconjugates," *Methods Mol. Biol.* 298: 209-223 (2005).

(Continued)

*Primary Examiner* — Nianxiang Zou
(74) *Attorney, Agent, or Firm* — Leydig, Voit & Mayer

(57) ABSTRACT

Disclosed is a T cell receptor (TCR) having antigenic specificity for an HLA-A2-restricted epitope of human papillomavirus (HPV) 16 E6, $E6_{29-38}$. Related polypeptides and proteins, as well as related nucleic acids, recombinant expression vectors, host cells, and populations of cells are also provided. Antibodies, or an antigen binding portion thereof, and pharmaceutical compositions relating to the TCRs of the invention are also provided. Also disclosed are methods of detecting the presence of a condition in a mammal and methods of treating or preventing a condition in a mammal, wherein the condition is cancer, HPV 16 infection, or HPV-positive premalignancy.

20 Claims, 6 Drawing Sheets

Specification includes a Sequence Listing.

(56) References Cited

OTHER PUBLICATIONS

Huse et al., "Generation of a Large Combinatorial Library of the Immunoglobulin Repertoire in Phage Lambda," *Science*, 246, 1275-81 (1989).
Kirin et al., "Amino Acid and Peptide Bioconjugates of Copper (II) and Zinc (II) Complexes with a Modified N,N-Bis(2-picolyl)amine Ligand," *Inorg Chem.* 44(15): 5405-5415 (2005).
Köhler et al., "Derivation of specific antibody-producing tissue culture and tumor lines by cell fusion," *Eur. J. Immunol.*, 5, 511-519 (1976).
Lyons, "Immunotherapeutic strategies against human papillomavirus induced cervical cancer," A Dissertation Submitted to the Faculty of the Graduate School in Candidacy for the Degree of Doctor of Philosophy, Program in Molecular Biology, Chicago, IL (2004).
Pedersen et al., "Comparison of surface accessible residues in human and murine immunoglobulin Fv domains. Implication for humanization of murine antibodies," *J. Mol. Biol.*, 235, 959-973 (1994).
Reiter et al., "Engineering interchain disulfide bonds into conserved framework regions of Fv fragments: improved biochemical characteristics of recombinant immunotoxins containing disulfide-stabilized Fv," *Protein Engineering*, 7, 697-704 (1994).
Riddell et al., "The use of anti-CD3 and anti-CD28 monoclonal antibodies to clone and expand human antigen-specific T-cells," *J. Immunol. Methods*, 128: 189-201 (1990).
Roder et al., "The EBV-Hybridoma Techique," *Methods Enzymol.*, 121, 140-67 (1986).
Scholten et al., "Promiscuous behavior of HPV16E6 specific T cell receptor beta chains hampers functional expression in TCR transgenic T cells, which can be restored in part by genetic modification," *Cell Oncol.*, 32: 43-56 (2010).
Scholten et al., "Preservation and redirection of HPV16E7-specific T cell receptors for immunotherapy of cervical cancer," *Clin Immunol.*, 114: 119-29 (2005).
Scholten et al., "Generating HPV specific T helper cells for the treatment of HPV induced malignancies using TCR gene transfer," *J. Translation. Med.*, 9: 147 (2011).
Thomas et al., "HPV16 E6$_{29-38}$-specific T cells kill cervical carcinoma cells despite partial evasion of T-cell effector function," *Int. J. Cancer*, 122: 2791-99 (2008).
Wadhwa et al., "Receptor Mediated Glycotargeting," *J. Drug Targeting* 3: 111 (1995).
Murphy et al., "T-cell receptors concentrate diversity in the third hypervariable region," *Janeway's Immunobiology*, 7th Edition, p. 157-158 (2008).

* cited by examiner ately extracted and the extracted RNA was reverse transcribed to cDNA. The full-length alpha and beta chains of the HPV 16 E6 TCR were amplified by polymerase chain reaction (PCR). The TCR alpha and beta chain sequences were then linked by a furin SGSG P2A linker and cloned into a MSGV1 retroviral vector

SEQUENCE LISTING

<160> NUMBER OF SEQ ID NOS: 39

<210> SEQ ID NO 1

```
<211> LENGTH: 158
<212> TYPE: PRT
<213> ORGANISM: Artificial Sequence
<220> FEATURE:
<223> OTHER INFORMATION: Synthetic

<400> SEQUENCE: 1

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Thr Ile His Asp Ile Ile Leu Glu Cys Val
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Ser Ile Phe Asn Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Leu Tyr Lys Ala Gly Glu Leu
1               5

<210> SEQ ID NO 5
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 5

Ala Gly His Pro Ser Ser Asn Ser Gly Tyr Ala Leu Asn
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ser Gly His Val Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Phe Asn Tyr Glu Ala Gln
1               5

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Ala Ser Ser Ser Gln Thr Gly Ala Arg Thr Asp Thr Gln Tyr
1               5                   10

<210> SEQ ID NO 9
<211> LENGTH: 131
<212> TYPE: PRT
<213> ORGANISM: Artificial Sequence
<220> FEATURE:
<223> OTHER INFORMATION: Synthetic

<400> SEQUENCE: 9

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly His Pro Ser
```

```
                100                 105                 110
Ser Asn Ser Gly Tyr Ala Leu Asn Phe Gly Lys Gly Thr Ser Leu Leu
            115                 120                 125

Val Thr Pro
    130

<210> SEQ ID NO 10
<211> LENGTH: 135
<212> TYPE: PRT
<213> ORGANISM: Artificial Sequence
<220> FEATURE:
<223> OTHER INFORMATION: Synthetic

<400> SEQUENCE: 10

Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser Ser Gln Thr Gly Ala Arg Thr Asp Thr Gln Tyr Phe Gly Pro
        115                 120                 125

Gly Thr Arg Leu Thr Val Leu
    130                 135

<210> SEQ ID NO 11
<211> LENGTH: 272
<212> TYPE: PRT
<213> ORGANISM: Artificial Sequence
<220> FEATURE:
<223> OTHER INFORMATION: Synthetic

<400> SEQUENCE: 11

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly His Pro Ser
            100                 105                 110

Ser Asn Ser Gly Tyr Ala Leu Asn Phe Gly Lys Gly Thr Ser Leu Leu
        115                 120                 125
```

```
Val Thr Pro His Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 12
<211> LENGTH: 314
<212> TYPE: PRT
<213> ORGANISM: Artificial Sequence
<220> FEATURE:
<223> OTHER INFORMATION: Synthetic

<400> SEQUENCE: 12

Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser Ser Gln Thr Gly Ala Arg Thr Asp Thr Gln Tyr Phe Gly Pro
        115                 120                 125

Gly Thr Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220
```

```
Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Glu Ser
        260                 265                 270

Tyr Gln Gln Gly Val Leu Ser Ala Thr Ile Leu Tyr Glu Ile Leu Leu
    275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310
```

<210> SEQ ID NO 13
<211> LENGTH: 141
<212> TYPE: PRT
<213> ORGANISM: Artificial Sequence
<220> FEATURE:
<223> OTHER INFORMATION: Synthetic

<400> SEQUENCE: 13

```
His Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

<210> SEQ ID NO 14
<211> LENGTH: 179
<212> TYPE: PRT
<213> ORGANISM: Artificial Sequence
<220> FEATURE:
<223> OTHER INFORMATION: Synthetic

<400> SEQUENCE: 14

```
Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80
```

```
Arg Val Ser Ala Thr Phe Trp Gln Asn Pro Arg Asn His Phe Arg Cys
            85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 15
<211> LENGTH: 137
<212> TYPE: PRT
<213> ORGANISM: Artificial Sequence
<220> FEATURE:
<223> OTHER INFORMATION: Synthetic

<400> SEQUENCE: 15

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
                100                 105                 110

Val Met Gly Leu Arg Ile Leu Leu Leu Lys Val Ala Gly Phe Asn Leu
            115                 120                 125

Leu Met Thr Leu Arg Leu Trp Ser Ser
        130                 135

<210> SEQ ID NO 16
<211> LENGTH: 173
<212> TYPE: PRT
<213> ORGANISM: Artificial Sequence
<220> FEATURE:
<223> OTHER INFORMATION: Synthetic

<400> SEQUENCE: 16

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Ser Thr Asp Pro Gln Ala Tyr Lys
    50                  55                  60
```

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 17
<211> LENGTH: 268
<212> TYPE: PRT
<213> ORGANISM: Artificial Sequence
<220> FEATURE:
<223> OTHER INFORMATION: Synthetic

<400> SEQUENCE: 17

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly His Pro Ser
            100                 105                 110

Ser Asn Ser Gly Tyr Ala Leu Asn Phe Gly Lys Gly Thr Ser Leu Leu
        115                 120                 125

Val Thr Pro Asp Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

```
Phe Asn Leu Leu Met Thr Leu Arg Leu Trp Ser Ser
            260                 265

<210> SEQ ID NO 18
<211> LENGTH: 308
<212> TYPE: PRT
<213> ORGANISM: Artificial Sequence
<220> FEATURE:
<223> OTHER INFORMATION: Synthetic

<400> SEQUENCE: 18

Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser Ser Gln Thr Gly Ala Arg Thr Asp Thr Gln Tyr Phe Gly Pro
        115                 120                 125

Gly Thr Arg Leu Thr Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser
305

<210> SEQ ID NO 19
<211> LENGTH: 393
<212> TYPE: DNA
<213> ORGANISM: Artificial Sequence
```

<220> FEATURE:
<223> OTHER INFORMATION: Synthetic

<400> SEQUENCE: 19

| | | | | | |
|---|---|---|---|---|---|
| atgctccttg | aacatttatt | aataatcttg | tggatgcagc | tgacatgggt | cagtggtcaa | 60 |
| cagctgaatc | agagtcctca | atctatgttt | atccaggaag | gagaagatgt | ctccatgaac | 120 |
| tgcacttctt | caagcatatt | taacacctgg | ctatggtaca | agcaggaccc | tggggaaggt | 180 |
| cctgtcctct | tgatagcctt | atataaggct | ggtgaattga | cctcaaatgg | aagactgact | 240 |
| gctcagtttg | gtataaccag | aaaggacagc | ttcctgaata | tctcagcatc | catacctagt | 300 |
| gatgtaggca | tctacttctg | tgctgggcac | ccttcctcaa | attccgggta | tgcactcaac | 360 |
| ttcggcaaag | gcacctcgct | gttggtcaca | ccc | | | 393 |

<210> SEQ ID NO 20
<211> LENGTH: 405
<212> TYPE: DNA
<213> ORGANISM: Artificial Sequence
<220> FEATURE:
<223> OTHER INFORMATION: Synthetic

<400> SEQUENCE: 20

| | | | | | |
|---|---|---|---|---|---|
| atgggcacca | gtctcctatg | ctgggtggtc | ctgggtttcc | tagggacaga | tcacacaggt | 60 |
| gctggagtct | cccagtctcc | caggtacaaa | gtcacaaaga | ggggacagga | tgtagctctc | 120 |
| aggtgtgatc | caatttcggg | tcatgtatcc | ctttattggt | accgacaggc | cctggggcag | 180 |
| ggcccagagt | ttctgactta | cttcaattat | gaagcccaac | aagacaaatc | agggctgccc | 240 |
| aatgatcggt | tctctgcaga | gaggcctgag | ggatccatct | ccactctgac | gatccagcgc | 300 |
| acagagcagc | gggactcggc | catgtatcgc | tgtgccagca | gctcccagac | aggggcccgc | 360 |
| acagatacgc | agtattttgg | cccaggcacc | cggctgacag | tgctc | | 405 |

<210> SEQ ID NO 21
<211> LENGTH: 819
<212> TYPE: DNA
<213> ORGANISM: Artificial Sequence
<220> FEATURE:
<223> OTHER INFORMATION: Synthetic

<400> SEQUENCE: 21

| | | | | | |
|---|---|---|---|---|---|
| atgctccttg | aacatttatt | aataatcttg | tggatgcagc | tgacatgggt | cagtggtcaa | 60 |
| cagctgaatc | agagtcctca | atctatgttt | atccaggaag | gagaagatgt | ctccatgaac | 120 |
| tgcacttctt | caagcatatt | taacacctgg | ctatggtaca | agcaggaccc | tggggaaggt | 180 |
| cctgtcctct | tgatagcctt | atataaggct | ggtgaattga | cctcaaatgg | aagactgact | 240 |
| gctcagtttg | gtataaccag | aaaggacagc | ttcctgaata | tctcagcatc | catacctagt | 300 |
| gatgtaggca | tctacttctg | tgctgggcac | ccttcctcaa | attccgggta | tgcactcaac | 360 |
| ttcggcaaag | gcacctcgct | gttggtcaca | ccccatatcc | agaaccctga | ccctgccgtg | 420 |
| taccagctga | gagactctaa | atccagtgac | aagtctgtct | gcctattcac | cgattttgat | 480 |
| tctcaaacaa | atgtgtcaca | aagtaaggat | tctgatgtgt | atatcacaga | caaaactgtg | 540 |
| ctagacatga | ggtctatgga | cttcaagagc | aacagtgctg | tggcctggag | caacaaatct | 600 |
| gactttgcat | gtgcaaacgc | cttcaacaac | agcattattc | cagaagacac | cttcttcccc | 660 |
| agcccagaaa | gttcctgtga | tgtcaagctg | gtcgagaaaa | gctttgaaac | agatacgaac | 720 |
| ctaaactttc | aaaacctgtc | agtgattggg | ttccgaatcc | tcctcctgaa | agtggccggg | 780 | tttaatctgc tcatgacgct gcggctgtgg tccagctga                                819

<210> SEQ ID NO 22
<211> LENGTH: 945
<212> TYPE: DNA
<213> ORGANISM: Artificial Sequence
<220> FEATURE:
<223> OTHER INFORMATION: Synthetic

<400> SEQUENCE: 22
atgggcacca gtctcctatg ctgggtggtc ctgggtttcc tagggacaga tcacacaggt    60
gctggagtct cccagtctcc caggtacaaa gtcacaaaga ggggacagga tgtagctctc   120
aggtgtgatc caatttcggg tcatgtatcc ctttattggt accgacaggc cctggggcag   180
ggcccagagt ttctgactta cttcaattat gaagcccaac aagacaaatc agggctgccc   240
aatgatcggt tctctgcaga gaggcctgag ggatccatct ccactctgac gatccagcgc   300
acagagcagc gggactcggc catgtatcgc tgtgccagca gctcccagac aggggccccgc  360
acagatacgc agtattttgg cccaggcacc cggctgacag tgctcgagga cctgaaaaac   420
gtgttcccac ccgaggtcgc tgtgtttgag ccatcagaag cagagatctc ccacacccaa   480
aaggccacac tggtgtgcct ggccacaggc ttctaccccg accacgtgga gctgagctgg   540
tgggtgaatg ggaaggaggt gcacagtggg gtcagcacag acccgcagcc cctcaaggag   600
cagccccgccc tcaatgactc cagatactgc ctgagcagcc gctgagggt ctcggccacc   660
ttctggcaga accccgcaa ccacttccgc tgtcaagtcc agttctacgg gctctcggag    720
aatgacgagt ggacccagga tagggccaaa cctgtcaccc agatcgtcag cgccgaggcc   780
tggggtagag cagactgtgg cttcacctcc gagtcttacc agcaagggggt cctgtctgcc  840
accatcctct atgagatctt gctagggaag gccaccttgt atgccgtgct ggtcagtgcc   900
ctcgtgctga tggccatggt caagagaaag gattccagag gctag                   945

<210> SEQ ID NO 23
<211> LENGTH: 426
<212> TYPE: DNA
<213> ORGANISM: Artificial Sequence
<220> FEATURE:
<223> OTHER INFORMATION: Synthetic

<400> SEQUENCE: 23
catatccaga accctgaccc tgccgtgtac cagctgagag actctaaatc cagtgacaag    60
tctgtctgcc tattcaccga ttttgattct caaacaaatg tgtcacaaag taaggattct   120
gatgtgtata tcacagacaa aactgtgcta gacatgaggt ctatggactt caagagcaac   180
agtgctgtgg cctggagcaa caaatctgac tttgcatgtg caaacgcctt caacaacagc   240
attattccag aagacacctt cttccccagc ccagaaagtt cctgtgatgt caagctggtc   300
gagaaaagct ttgaaacaga tacgaaccta aactttcaaa acctgtcagt gattgggttc   360
cgaatcctcc tcctgaaagt ggccgggttt aatctgctca tgacgctgcg gctgtggtcc  420
agctga                                                             426

<210> SEQ ID NO 24
<211> LENGTH: 540
<212> TYPE: DNA
<213> ORGANISM: Artificial Sequence
<220> FEATURE:
<223> OTHER INFORMATION: Synthetic

<400> SEQUENCE: 24

```
gaggacctga aaaacgtgtt cccacccgag gtcgctgtgt ttgagccatc agaagcagag      60
atctcccaca cccaaaaggc cacactggtg tgcctggcca caggcttcta ccccgaccac     120
gtggagctga gctggtgggt gaatgggaag gaggtgcaca gtggggtcag cacagacccg     180
cagcccctca aggagcagcc cgccctcaat gactccagat actgcctgag cagccgcctg     240
agggtctcgg ccaccttctg gcagaacccc cgcaaccact tccgctgtca agtccagttc     300
tacgggctct cggagaatga cgagtggacc caggataggg ccaaacctgt cacccagatc     360
gtcagcgccg aggcctgggg tagagcagac tgtggcttca cctccgagtc ttaccagcaa     420
ggggtcctgt ctgccaccat cctctatgag atcttgctag gaaggccac  cttgtatgcc     480 gtgctggtca gtgccctcgt gctgatggcc atggtcaaga gaaaggattc cagaggctag     540
```

```
<210> SEQ ID NO 25
<211> LENGTH: 414
<212> TYPE: DNA
<213> ORGANISM: Artificial Sequence
<220> FEATURE:
<223> OTHER INFORMATION: Synthetic

<400> SEQUENCE: 25
```

```
gacatccaga acccagaacc tgctgtgtac cagttaaaag atcctcggtc tcaggacagc      60
accctctgcc tgttcaccga cttttgactcc caaatcaatg tgccgaaaac catgaatct     120 ggaacgttca tcactgacaa aactgtgctg acatgaaag ctatggattc caagagcaat      180
ggggccattg cctggagcaa ccagacaagc ttcacctgcc aagatatctt caaagagacc     240
aacgccacct accccagttc agacgttccc tgtgatgcca cgttgactga aaaagctttt     300
gaaacagata tgaacctaaa ctttcaaaac ctgtcagtta tgggactccg aatcctcctg     360
ctgaaagtag ccggatttaa cctgctcatg acgctgaggc tgtggtccag ttga           414
```

```
<210> SEQ ID NO 26
<211> LENGTH: 522
<212> TYPE: DNA
<213> ORGANISM: Artificial Sequence
<220> FEATURE:
<223> OTHER INFORMATION: Synthetic

<400> SEQUENCE: 26
```

```
gaggatctga aaatgtgac tccacccaag gtctccttgt ttgagccatc aaaagcagag       60
attgcaaaca acaaaaggc taccctcgtg tgcttggcca ggggcttctt ccctgaccac     120
gtggagctga gctggtgggt gaatggcaag gaggtccaca gtggggtcag cacggaccct     180
caggcctaca aggagagcaa ttatagctac tgcctgagca gccgcctgag ggtctctgct     240
accttctggc acaatcctcg caaccacttc cgctgccaag tgcagttcca tgggctttca     300
gaggaggaca gtggccaga gggctcaccc aaacctgtca cacagaacat cagtgcagag      360
gcctggggcc gagcagactg tgggattacc tcagcatcct atcaacaagg ggtcttgtct     420
gccaccatcc tctatgagat cctgctaggg aaagccaccc tgtatgctgt gcttgtcagt     480
acactggtgg tgatggctat ggtcaaaaga aagaattcat ga                        522
```

```
<210> SEQ ID NO 27
<211> LENGTH: 807
<212> TYPE: DNA
<213> ORGANISM: Artificial Sequence
<220> FEATURE:
<223> OTHER INFORMATION: Synthetic
```

<400> SEQUENCE: 27

```
atgctccttg aacatttatt aataatcttg tggatgcagc tgacatgggt cagtggtcaa     60
cagctgaatc agagtcctca atctatgttt atccaggaag gagaagatgt ctccatgaac    120
tgcacttctt caagcatatt taacacctgg ctatggtaca agcaggaccc tggggaaggt    180
cctgtcctct tgatagcctt atataaggct ggtgaattga cctcaaatgg aagactgact    240
gctcagtttg gtataaccag aaaggacagc ttcctgaata tctcagcatc catacctagt    300
gatgtaggca tctacttctg tgctgggcac ccttcctcaa attccgggta tgcactcaac    360
ttcggcaaag gcacctcgct gttggtcaca cccgacatcc agaacccaga acctgctgtg    420
taccagttaa aagatcctcg gtctcaggac agcaccctct gcctgttcac cgactttgac    480
tcccaaatca atgtgccgaa aaccatggaa tctggaacgt tcatcactga caaaactgtg    540
ctggacatga aagctatgga ttccaagagc aatggggcca ttgcctggag caaccagaca    600
agcttcacct gccaagatat cttcaaagag accaacgcca cctacccag ttcagacgtt    660
ccctgtgatg ccacgttgac tgagaaaagc tttgaaacag atatgaacct aaactttcaa    720
aacctgtcag ttatgggact ccgaatcctc ctgctgaaag tagccggatt taacctgctc    780
atgacgctga ggctgtggtc cagttga                                         807
```

<210> SEQ ID NO 28
<211> LENGTH: 927
<212> TYPE: DNA
<213> ORGANISM: Artificial Sequence
<220> FEATURE:
<223> OTHER INFORMATION: Synthetic'

<400> SEQUENCE: 28

```
atgggcacca gtctcctatg ctgggtggtc ctgggtttcc tagggacaga tcacacaggt     60
gctggagtct cccagtctcc caggtacaaa gtcacaaaga ggggacagga tgtagctctc    120
aggtgtgatc caatttcggg tcatgtatcc ctttattggt accgacaggc cctggggcag    180
ggcccagagt ttctgactta cttcaattat gaagcccaac aagacaaatc agggctgccc    240
aatgatcggt tctctgcaga gaggcctgag ggatccatct ccactctgac gatccagcgc    300
acagagcagc gggactcggc catgtatcgc tgtgccagca gctcccagac aggggcccgc    360
acagatacgc agtattttgg cccaggcacc cggctgacag tgctcgagga tctgagaaat    420
gtgactccac ccaaggtctc cttgtttgag ccatcaaaag cagagattgc aaacaaacaa    480
aaggctaccc tcgtgtgctt ggccaggggc ttcttccctg accacgtgga gctgagctgg    540
tgggtgaatg gcaaggaggt ccacagtggg gtcagcacgg accctcaggc ctacaaggag    600
agcaattata gctactgcct gagcagccgc ctgagggtct ctgctacctt ctggcacaat    660
cctcgcaacc acttccgctg ccaagtgcag ttccatgggc tttcagagga ggacaagtgg    720
ccagagggct cacccaaacc tgtcacacag aacatcagtg cagaggcctg ggccgagca    780
gactgtggga ttacctcagc atcctatcaa caagggtct tgtctgccac catcctctat    840
gagatcctgc tagggaaagc caccctgtat gctgtgcttg tcagtacact ggtggtgatg    900
gctatggtca aagaaagaa ttcatga                                         927
```

<210> SEQ ID NO 29
<211> LENGTH: 1815
<212> TYPE: DNA
<213> ORGANISM: Artificial Sequence
<220> FEATURE:
<223> OTHER INFORMATION: Synthetic

<400> SEQUENCE: 29

```
atggcccttg aacatctgtt gataatactg tggatgcaac ttacctgggt atctggtcag       60
caattgaacc agtctccaca gtccatgttt atccaagaag gggaggacgt gtccatgaat      120
tgtacaagct ccagtatctt caacacgtgg ctgtggtaca acaggatcc tggggaagga      180
ccagtactgt tgatagccct ctataaggcg ggcgaactga catccaatgg aagactcaca      240
gcccaattcg gaattacccg gaaggattct ttcctcaaca tctccgcgag tattccatct      300
gatgtaggaa tatacttctg tgcagggcat ccgtctagca acagtggata tgccctcaat      360
tttggaaagg gcacctccct gctggttacc ccagacattc agaaccccga accagccgta      420
tatcagttga aggacccaag atctcaggat agtacactct gtttgtttac ggactttgac      480
tcacaaatca acgtcccgaa gactatgaaa gtggtacgt tcatcacaga taagacggtt      540
ctggacatga aggctatgga ctcaaagagc aacgggcaa ttgcttggtc caaccagaca      600
agctttacct gtcaggacat ttttaaggag actaatgcta cttatccctc agcgacgtt       660
ccgtgtgatg cgactcttac cgagaagtct tttgagaccg atatgaatct caacttccag      720
aatctgtcag tgatgggtct gcggatcctg cttctgaagg ttgcaggatt caatcttctt      780
atgactctcc ggctctggtc ttcaagagcc aaaagaagtg gttctggcgc gacgaatttt      840
agtttgctta gcaagccgg agatgtggag gaaaatcctg gaccgatggg cacaagtttg       900
ctgtgctggg ttgtgttggg cttctgggt acagatcata ctgggcggg agtctctcaa       960
agcccccgat acaaagtcac taaaagaggg caggatgtcg cgcttcgctg tgatcccatt     1020
agcgggcatg tctcccttta ttggtaccgg caggctttgg gacaaggacc ggagttcctc     1080
acttacttca actacgaagc gcagcaggac aagtccggtc tgcctaatga tagattcagc     1140
gccgagagac cggagggcag tatctctact cttacgatac aaagaacgga gcagcgagac     1200
tctgctatgt atagatgtgc aagttctagc cagacgggtg ctcgcacgga cactcaatat     1260
ttcggtcctg gtacaagatt gaccgtcttg gaggatctcc ggaacgtcac cccaccaaag     1320
gtcagtttgt ttgagccatc aaaggcggag atcgccaaca acagaaagc tacgctcgtg     1380
tgtttggctc ggggcttctt cccagaccac gtagaacttt cctggtgggt caatggaaag     1440
gaggttcatt ccggagtgtc cactgatccc caagcgtaca aggaatccaa ctatagctac     1500
tgtctctcat ctcggctccg ggtgagtgcg acattctggc ataatcctcg gaaccacttt     1560
cgatgccaag tgcagtttca tgggttgagc gaggaagaca gtggcccga gggcagtcct     1620
aaaccagtca ctcaaaacat aagcgccgag gcatgggta gagccgattg tgggattact     1680
agcgcttcat accaacaagg ggtattgagc gctacaattc tttacgaaat tctcctcggc     1740
aaggcgacgc tctacgccgt actggtgtct actctcgtgg ttatggcaat ggtgaaacgg     1800
aaaaacagct aatga                                                     1815
```

<210> SEQ ID NO 30
<211> LENGTH: 7325
<212> TYPE: DNA
<213> ORGANISM: Artificial Sequence
<220> FEATURE:
<223> OTHER INFORMATION: Synthetic

<400> SEQUENCE: 30

```
ccatggccct tgaacatctg ttgataatac tgtggatgca acttacctgg gtatctggtc       60
agcaattgaa ccagtctcca cagtccatgt ttatccaaga aggggaggac gtgtccatga      120
```

```
attgtacaag ctccagtatc ttcaacacgt ggctgtggta caaacaggat cctggggaag      180
gaccagtact gttgatagcc ctctataagg cgggcgaact gacatccaat ggaagactca      240
cagcccaatt cggaattacc cggaaggatt ctttcctcaa catctccgcg agtattccat      300
ctgatgtagg aatatacttc tgtgcagggc atccgtctag caacagtgga tatgccctca      360
attttggaaa gggcacctcc ctgctggtta ccccagacat tcagaacccc gaaccagccg      420
tatatcagtt gaaggaccca agatctcagg atagtacact ctgtttgttt acggactttg      480
actcacaaat caacgtcccg aagactatgg aaagtggtac gttcatcaca gataagacgg      540
ttctggacat gaaggctatg gactcaaaga gcaacgggc aattgcttgg tccaaccaga      600
caagctttac ctgtcaggac attttttaagg agactaatgc tacttatccc tccagcgacg      660
ttccgtgtga tgcgactctt accgagaagt cttttgagac cgatatgaat ctcaacttcc      720
agaatctgtc agtgatgggt ctgcggatcc tgcttctgaa ggttgcagga ttcaatcttc      780
ttatgactct ccggctctgg tcttcaagag ccaaaagaag tggttctggc gcgacgaatt      840
ttagtttgct taagcaagcc ggagatgtgg aggaaaatcc tggaccgatg gcacaagtt      900 tgctgtgctg ggttgtgttg ggcttttctgg gtacagatca tactggggcg ggagtctctc      960
aaagcccccg atacaaagtc actaaaagag gcaggatgt cgcgcttcgc tgtgatccca     1020
ttagcgggca tgtctcccct tattggtacc ggcaggcttt gggacaagga ccggagttcc     1080
tcacttactt caactacgaa gcgcagcagg acaagtccgg tctgcctaat gatagattca     1140
gcgccgagag accggagggc agtatctcta ctcttacgat acaaagaacg gagcagcgag     1200
actctgctat gtatagatgt gcaagttcta gccagacggg tgctcgcacg gacactcaat     1260
atttcggtcc tggtacaaga ttgaccgtct tggaggatct ccggaacgtc accccaccaa     1320
aggtcagttt gtttgagcca tcaaaggcgg agatcgccaa caaacagaaa gctacgctcg     1380
tgtgtttggc tcggggcttc ttcccagacc acgtagaact ttcctggtgg gtcaatggaa     1440
aggaggttca ttccggagtg tccactgatc cccaagcgta caaggaatcc aactatagct     1500
actgtctctc atctcggctc cgggtgagtg cgacattctg gcataatcct cggaaccact     1560
ttcgatgcca agtgcagttt catgggttga gcgaggaaga caagtggccc gagggcagtc     1620
ctaaaccagt cactcaaaac ataagcgccg aggcatgggg tagagccgat tgtgggatta     1680
ctagcgcttc ataccaacaa ggggtattga gcgctacaat tctttacgaa attctcctcg     1740
gcaaggcgac gctctacgcc gtactggtgt ctactctcgt ggttatggca atggtgaaac     1800
ggaaaaacag ctaatgagaa ttctgcagtc gacggtaccg cgggcccggg atccgataaa     1860
ataaaagatt ttatttagtc tccagaaaaa ggggggaatg aaagacccca cctgtaggtt     1920
tggcaagcta gcttaagtaa cgccatttg caaggcatgg aaaatacata actgagaata     1980
gagaagttca gatcaaggtt aggaacagag agacagcaga atatgggcca aacaggatat     2040
ctgtggtaag cagttcctgc cccggctcag ggccaagaac agatggtccc cagatgcggt     2100
cccgccctca gcagtttcta gagaaccatc agatgtttcc agggtgcccc aaggacctga     2160
aaatgaccct gtgccttatt tgaactaacc aatcagttcg cttctcgctt ctgttcgcgc     2220
gcttctgctc cccgagctca ataaaagagc ccacaaccc tcactcggcg cgccagtcct     2280
ccgatagact gcgtcgcccg ggtacccgtg tatccaataa accctcttgc agttgcatcc     2340
gacttgtggt ctcgctgttc cttgggaggg tctcctctga gtgattgact acccgtcagc     2400
gggggtcttt catgggtaac agtttcttga agttggagaa caacattctg agggtaggag     2460
tcgaatatta agtaatcctg actcaattag ccactgtttt gaatccacat actccaatac     2520
```

```
tcctgaaatc catcgatgga gttcattatg gacagcgcag aaagagctgg ggagaattgt   2580
gaaattgtta tccgctcaca attccacaca acatacgagc cggaagcata aagtgtaaag   2640
cctggggtgc ctaatgagtg agctaactca cattaattgc gttgcgctca ctgcccgctt   2700
tccagtcggg aaacctgtcg tgccagctgc attaatgaat cggccaacgc gcggggagag   2760
gcggtttgcg tattgggcgc tcttccgctt cctcgctcac tgactcgctg cgctcggtcg   2820
ttcggctgcg cgagcggta tcagctcact caaaggcggt aatacggtta tccacagaat   2880
caggggataa cgcaggaaag aacatgtgag caaaaggcca gcaaaaggcc aggaaccgta   2940
aaaaggccgc gttgctggcg ttttttccata ggctccgccc ccctgacgag catcacaaaa   3000
atcgacgctc aagtcagagg tggcgaaacc cgacaggact ataaagatac caggcgtttc   3060
cccctggaag ctccctcgtg cgctctcctg ttccgaccct gccgcttacc ggatacctgt   3120
ccgcctttct cccttcggga agcgtggcgc tttctcatag ctcacgctgt aggtatctca   3180
gttcggtgta ggtcgttcgc tccaagctgg gctgtgtgca cgaaccccccc gttcagcccg   3240
accgctgcgc cttatccggt aactatcgtc ttgagtccaa cccggtaaga cacgacttat   3300
cgccactgga gcagccact ggtaacagga ttagcagagc gaggtatgta ggcggtgcta   3360
cagagttctt gaagtggtgg cctaactacg gctacactag aagaacagta tttggtatct   3420
gcgctctgct gaagccagtt accttcggaa aaagagttgg tagctcttga tccggcaaac   3480
aaaccaccgc tggtagcggt ggtttttttg tttgcaagca gcagattacg cgcagaaaaa   3540
aaggatctca agaagatcct ttgatctttt ctacggggtc tgacgctcag tggaacgaaa   3600
actcacgtta agggattttg gtcatgagat tatcaaaaag gatcttcacc tagatccttt   3660
taaattaaaa atgaagtttt aaatcaatct aaagtatata tgagtaaact tggtctgaca   3720
gttaccaatg cttaatcagt gaggcaccta tctcagcgat ctgtctattt cgttcatcca   3780
tagttgcctg actccccgtc gtgtagataa ctacgatacg ggagggctta ccatctggcc   3840
ccagtgctgc aatgataccg cgagacccac gctcaccggc tccagattta tcagcaataa   3900
accagccagc cggaagggcc gagcgcagaa gtggtcctgc aactttatcc gcctccatcc   3960
agtctattaa ttgttgccgg gaagctagag taagtagttc gccagttaat agtttgcgca   4020
acgttgttgc cattgctaca ggcatcgtgg tgtcacgctc gtcgtttggt atggcttcat   4080
tcagctccgg ttcccaacga tcaaggcgag ttacatgatc ccccatgttg tgcaaaaaag   4140
cggttagctc cttcggtcct ccgatcgttg tcagaagtaa gttggccgca gtgttatcac   4200
tcatggttat ggcagcactg cataattctc ttactgtcat gccatccgta agatgctttt   4260
ctgtgactgg tgagtactca accaagtcat tctgagaata gtgtatgcgg cgaccgagtt   4320
gctcttgccc ggcgtcaata cgggataata ccgcgccaca tagcagaact ttaaaagtgc   4380
tcatcattgg aaaacgttct cggggcgaa aactctcaag gatcttaccg ctgttgagat   4440
ccagttcgat gtaacccact cgtgcaccca actgatcttc agcatctttt actttcacca   4500
gcgtttctgg gtgagcaaaa acaggaaggc aaaatgccgc aaaaaaggga ataagggcga   4560
cacggaaatg ttgaatactc atactcttcc ttttcaata ttattgaagc atttatcagg   4620
gttattgtct catgagcgga tacatatttg aatgtatttt gaaaaataaa caataggggg   4680
ttccgcgcac atttccccga aaagtgccac ctgacgtcta agaaaccatt attatcatga   4740
cattaaccta taaaaatagg cgtatcacga ggccctttcg tctcgcgcgt ttcggtgatg   4800
acggtgaaaa cctctgacac atgcagctcc cggagacggt cacagcttgt ctgtaagcgg   4860
```

-continued

| | |
|---|---|
| atgccgggag cagacaagcc cgtcagggcg cgtcagcggg tgttggcggg tgtcgggget | 4920 |
| ggcttaacta tgcggcatca gagcagattg tactgagagt gcaccatatg cggtgtgaaa | 4980 |
| taccgcacag atgcgtaagg agaaaatacc gcatcaggcg ccattcgcca ttcaggctgc | 5040 |
| gcaactgttg ggaagggcga tcggtgcggg cctcttcgct attacgccag ctggcgaaag | 5100 |
| ggggatgtgc tgcaaggcga ttaagttggg taacgccagg gttttcccag tcacgacgtt | 5160 |
| gtaaaacgac ggcgcaagga atggtgcatg caaggagatg cgcccaaca gtcccccggc | 5220 |
| cacggggcct gccaccatac ccacgccgaa acaagcgctc atgagcccga gtggcgagc | 5280 |
| ccgatcttcc ccatcggtga tgtcggcgat ataggcgcca gaaccgcac ctgtggcgcc | 5340 |
| ggtgatgccg gccacgatgc gtccggcgta gaggcgatta gtccaatttg ttaaagacag | 5400 |
| gatatcagtg gtccaggctc tagttttgac tcaacaatat caccagctga agcctataga | 5460 |
| gtacgagcca tagataaaat aaaagatttt atttagtctc cagaaaaagg ggggaatgaa | 5520 |
| agaccccacc tgtaggtttg gcaagctagc ttaagtaacg ccattttgca aggcatggaa | 5580 |
| aatacataac tgagaataga gaagttcaga tcaaggttag gaacagagag acagcagaat | 5640 |
| atgggccaaa caggatatct gtggtaagca gttcctgccc cggctcaggg ccaagaacag | 5700 |
| atggtcccca gatgcggtcc cgccctcagc agtttctaga gaaccatcag atgtttccag | 5760 |
| ggtgccccaa ggacctgaaa tgaccctgtg ccttatttga actaaccaat cagttcgctt | 5820 |
| ctcgcttctg ttcgcgcgct tctgctcccc gagctcaata aaagagccca caccccctca | 5880 |
| ctcggcgcgc cagtcctccg atagactgcg tcgcccgggt accgtattc ccataaaagc | 5940 |
| ctcttgctgt ttgcatccga atcgtggact cgctgatcct tgggagggtc tcctcagatt | 6000 |
| gattgactgc ccacctcggg ggtctttcat ttggaggttc caccgagatt tggagacccc | 6060 |
| tgcccaggga ccaccgaccc ccccgccggg aggtaagctg gccagcggtc gtttcgtgtc | 6120 |
| tgtctctgtc tttgtgcgtg tttgtgccgg catctaatgt ttgcgcctgc gtctgtacta | 6180 |
| gttagctaac tagctctgta tctggcggac ccgtggtgga actgacgagt tcggaacacc | 6240 |
| cggccgcaac cctgggagac gtcccaggga cttcggggge cgttttgtg gcccgacctg | 6300 |
| agtcctaaaa tcccgatcgt ttaggactct ttggtgcacc cccttagag gagggatatg | 6360 |
| tggttctggt aggagacgag aacctaaaac agttcccgcc tccgtctgaa ttttgctttt | 6420 |
| cggtttggga ccgaagccgc gccgcgcgtc ttgtctgctg cagcatcgtt ctgtgttgtc | 6480 |
| tctgtctgac tgtgtttctg tatttgtctg aaaatatggg cccgggctag cctgttacca | 6540 |
| ctcccttaag tttgacctta ggtcactgga aagatgtcga gcggatcgct cacaaccagt | 6600 |
| cggtagatgt caagaagaga cgttgggtta ccttctgctc tgcagaatgg ccaaccttta | 6660 |
| acgtcggatg gccgcgagac ggcacccttta accgagacct catcacccag gttaagatca | 6720 |
| aggtcttttc acctggcccg catggacacc cagaccaggt ccctacatc gtgacctggg | 6780 |
| aagccttggc ttttgacccc cctccctggg tcaagccctt tgtacaccct aagcctccgc | 6840 |
| ctcctcttcc tccatccgcc ccgtctctcc cccttgaacc tcctcgttcg accccgcctc | 6900 |
| gatcctccct ttatccagcc ctcactcctt ctctaggcgc cccatatgg ccatatgaga | 6960 |
| tcttatatgg ggcaccccg cccttgtaa acttccctga cctgacatg acaagagtta | 7020 |
| ctaacagccc ctctctccaa gctcacttac aggctctcta cttagtccag cacgaagtct | 7080 |
| ggagacctct ggcggcagcc taccaagaac aactggaccg accggtggta cctcacccctt | 7140 |
| accgagtcgc cgacacagtg tgggtccgcc gacaccgac taagaaccta gaacctcgct | 7200 |
| ggaaaggacc ttacacagtc ctgctgacca ccccccaccgc cctcaaagta gacggcatcg | 7260 | cagcttggat acacgccgcc cacgtgaagg ctgccgaccc cggggtgga ccatcctcta    7320 gaccg                                                               7325

<210> SEQ ID NO 31
<211> LENGTH: 15
<212> TYPE: DNA
<213> ORGANISM: Artificial Sequence
<220> FEATURE:
<223> OTHER INFORMATION: Synthetic

<400> SEQUENCE: 31
agcatattta acacc                                                    15

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
ttatataagg ctggtgaatt g                                             21

<210> SEQ ID NO 33
<211> LENGTH: 39
<212> TYPE: DNA
<213> ORGANISM: Artificial Sequence
<220> FEATURE:
<223> OTHER INFORMATION: Synthetic

<400> SEQUENCE: 33
gctgggcacc cttcctcaaa ttccgggtat gcactcaac                          39

<210> SEQ ID NO 34
<211> LENGTH: 15
<212> TYPE: DNA
<213> ORGANISM: Artificial Sequence
<220> FEATURE:
<223> OTHER INFORMATION: Synthetic

<400> SEQUENCE: 34
tcgggtcatg tatcc                                                    15

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
ttcaattatg aagcccaa                                                 18

<210> SEQ ID NO 36
<211> LENGTH: 42
<212> TYPE: DNA
<213> ORGANISM: Artificial Sequence
<220> FEATURE:
<223> OTHER INFORMATION: Synthetic

<400> SEQUENCE: 36
gccagcagct cccagacagg ggcccgcaca gatacgcagt at                      42

<210> SEQ ID NO 37

```
<211> LENGTH: 27
<212> TYPE: PRT
<213> ORGANISM: Artificial Sequence
<220> FEATURE:
<223> OTHER INFORMATION: Synthetic

<400> SEQUENCE: 37

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 38
<211> LENGTH: 393
<212> TYPE: DNA
<213> ORGANISM: Artificial Sequence
<220> FEATURE:
<223> OTHER INFORMATION: Synthetic

<400> SEQUENCE: 38
atggcccttg aacatctgtt gataatactg tggatgcaac ttacctgggt atctggtcag    60
caattgaacc agtctccaca gtccatgttt atccaagaag gggaggacgt gtccatgaat   120
tgtacaagct ccagtatctt caacacgtgg ctgtggtaca acaggatcc tggggaagga   180 ccagtactgt tgatagccct ctataaggcg ggcgaactga catccaatgg aagactcaca   240
gcccaattcg gaattacccg gaaggattct ttcctcaaca tctccgcgag tattccatct   300
gatgtaggaa tatacttctg tgcagggcat ccgtctagca acagtggata tgccctcaat   360
tttggaaagg gcacctccct gctggttacc cca                               393

<210> SEQ ID NO 39
<211> LENGTH: 405
<212> TYPE: DNA
<213> ORGANISM: Artificial Sequence
<220> FEATURE:
<223> OTHER INFORMATION: Synthetic

<400> SEQUENCE: 39
atgggcacaa gtttgctgtg ctgggttgtg ttgggctttc tgggtacaga tcatactggg    60
gcgggagtct ctcaaagccc ccgatacaaa gtcactaaaa gagggcagga tgtcgcgctt   120
cgctgtgatc ccattagcgg gcatgtctcc ctttattggt accggcaggc tttgggacaa   180
ggaccggagt tcctcactta cttcaactac gaagcgcagc aggacaagtc cggtctgcct   240
aatgatagat tcagcgccga gaccggag ggcagtatct ctactcttac gatacaaaga   300
acggagcagc gagactctgc tatgtataga tgtgcaagtt ctagccagac gggtgctcgc   360
acggacactc aatatttcgg tcctggtaca agattgaccg tcttg                   405
```

ANTI-HUMAN PAPILLOMAVIRUS 16 E6 T CELL RECEPTORS

CROSS-REFERENCE TO RELATED APPLICATIONS

This patent application is a continuation of U.S. application Ser. No. 14/905,108, filed Jan. 14, 2016, which is the U.S. national phase of International Patent Application No. PCT/US2014/046480, filed Jul. 14, 2014, which claims the benefit of U.S. Provisional Patent Application No. 61/846,167, filed Jul. 15, 2013, each of which is incorporated herein by reference in its entirety.

STATEMENT REGARDING FEDERALLY SPONSORED RESEARCH AND DEVELOPMENT

This invention was made with Government support under project numbers ZIABC011477 and BC010984-5 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 46,045 Byte ASCII (Text) file named "730735_ST25.TXT" Sep. 25, 2017.

BACKGROUND OF THE INVENTION

The primary cause of some cancer types such as, for example, uterine cervical cancer, is human papillomavirus (HPV) infection. Despite advances in treatments such as chemotherapy, the prognosis for many cancers, including HPV-associated cancers, may be poor. Accordingly, there exists an unmet need for additional treatments for cancer, particularly HPV-associated cancers.

BRIEF SUMMARY OF THE INVENTION

An embodiment of the invention provides a T cell receptor (TCR) having antigenic specificity for human papillomavirus (HPV) 16 E6 and comprising a human variable region and a murine constant region.

Another embodiment of the invention provides an isolated or purified TCR having antigenic specificity for HPV 16 E6 and comprising the amino acid sequences of SEQ ID NOs: 3-8.

The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs (including functional portions and functional variants thereof) of the invention.

Methods of detecting the presence of a condition in a mammal and methods of treating or preventing a condition in a mammal, wherein the condition is cancer, HPV 16 infection, or HPV-positive premalignancy, are further provided by the invention. The inventive method of detecting the presence of a condition in a mammal comprises (i) contacting a sample comprising cells of the condition with any of the inventive TCRs (including functional portions and functional variants thereof), polypeptides, proteins, nucleic acids, recombinant expression vectors, host cells, populations of host cells, antibodies, or antigen binding portions thereof, or pharmaceutical compositions described herein, thereby forming a complex, and (ii) detecting the complex, wherein detection of the complex is indicative of the presence of the condition in the mammal, wherein the condition is cancer, HPV 16 infection, or HPV-positive premalignancy.

The inventive method of treating or preventing a condition in a mammal comprises administering to the mammal any of the TCRs (including functional portions and functional variants thereof), polypeptides, or proteins described herein, any nucleic acid or recombinant expression vector comprising a nucleotide sequence encoding any of the TCRs (including functional portions and functional variants thereof), polypeptides, proteins described herein, or any host cell or population of host cells comprising a recombinant vector which encodes any of the TCRs (including functional portions and functional variants thereof), polypeptides, or proteins described herein, in an amount effective to treat or prevent the condition in the mammal, wherein the condition is cancer, HPV 16 infection, or HPV-positive premalignancy.

DETAILED DESCRIPTION OF THE INVENTION

Figure 1:
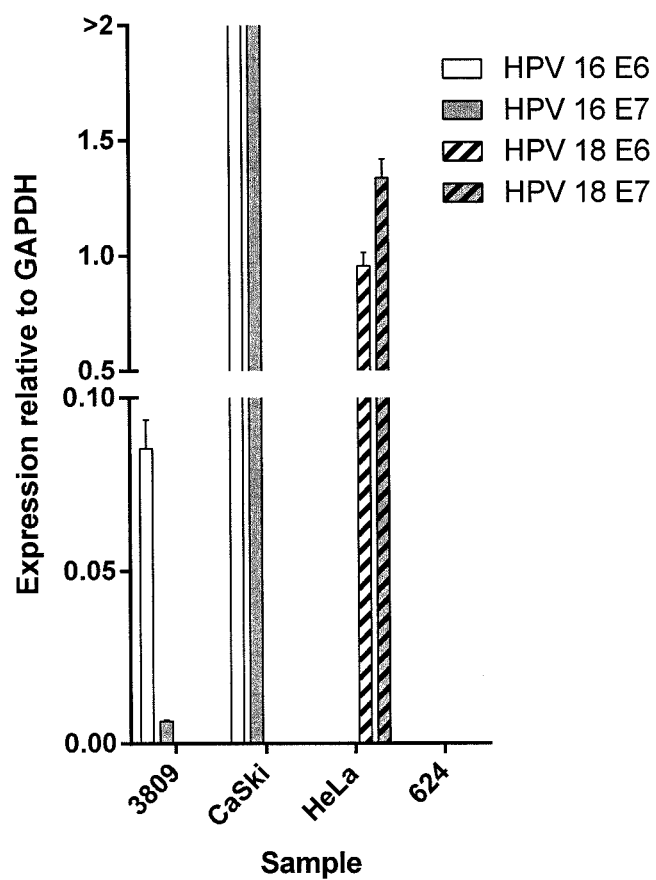
FIG. 1 is a bar graph showing expression of HPV 16 E6 (white bars), HPV 16 E7 (shaded unhatched bars), HPV 18 E6 (unshaded hatched bars), or HPV 18 E7 (shaded hatched bars) relative to glyceraldehyde 3-phosphate dehydrogenase (GAPDH) expression by CaSki cells, HeLa cells, 624 cells, or cells from tumor 3809.

An embodiment of the invention provides a T cell receptor (TCR), and functional portions and functional variants thereof, having antigenic specificity for human papillomavirus (HPV) 16 E6 and comprising a human variable region and a murine constant region. In an embodiment of the invention, the TCR has antigenic specificity for HPV 16 $E6_{29-38}$.

The HPV 16 is the subtype of HPV that is most commonly associated with malignancy. Without being bound to a particular theory or mechanism, HPV 16 is believed to cause cancer at least partly through the actions of the oncoprotein E6, which deregulates cell cycle control. HPV 16 E6 is constitutively expressed in cancer cells and is not expressed by normal, uninfected human tissues. HPV 16 E6 is expressed in a variety of human cancers including, but not limited to, cancer of the uterine cervix, oropharynx, anus, anal canal, anorectum, vagina, vulva, and penis.

The TCR may have antigenic specificity for any HPV 16 E6 protein, polypeptide or peptide. In an embodiment of the invention, the TCR has antigenic specificity for a HPV 16 E6 protein comprising, consisting of, or consisting essentially of, the amino acid sequence of SEQ ID NO: 1. In a preferred embodiment of the invention, the TCR has antigenic specificity for a HPV 16 $E6_{29-38}$ peptide comprising, consisting of, or consisting essentially of, the amino acid sequence of TIHDIILECV (SEQ ID NO: 2).

In an embodiment of the invention, the inventive TCRs are able to recognize HPV 16 E6 in a major histocompatibility complex (MHC) class I-dependent manner. "MHC class I-dependent manner," as used herein, means that the TCR elicits an immune response upon binding to HPV 16 E6 within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The TCRs (including functional portions and functional variants thereof) of the invention provide many advantages, including when expressed by cells used for adoptive cell transfer. Without being bound by a particular theory or mechanism, it is believed that because HPV 16 E6 is expressed by HPV 16-infected cells of multiple cancer types, the inventive TCRs (including functional portions and functional variants thereof) advantageously provide the ability to destroy cells of multiple types of HPV 16-associated cancer and, accordingly, treat or prevent multiple types of HPV 16-associated cancer. Additionally, without being bound to a particular theory or mechanism, it is believed that because the HPV 16 E6 protein is expressed only in cancer cells, HPV 16-infected cells, or HPV-positive premalignancy cells, the inventive TCRs (including functional portions and functional variants thereof) advantageously target the destruction of cancer cells, HPV 16-infected cells, or HPV-positive premalignancy cells, while minimizing or eliminating the destruction of nothial, non-cancerous, non-HPV-infected, and non-HPV-positive premalignant cells, thereby reducing, for example, by minimizing or eliminating, toxicity. Moreover, the inventive TCRs may, advantageously, successfully treat or prevent HPV-positive cancers that do not respond to other types of treatment such as, for example, chemotherapy alone, surgery, or radiation. Additionally, the inventive TCRs provide highly avid recognition of HPV 16 E6, which may, advantageously, provide the ability to recognize unmanipulated tumor cells (e.g., tumor cells that have not been treated with interferon-gamma, transfected with a vector encoding one or both of HPV 16 E6 and HLA-A2, pulsed with the $E6_{29-38}$ peptide, or a combination thereof).

The phrase "antigenic specificity," as used herein, means that the TCR can specifically bind to and immunologically recognize HPV 16 E6 with high avidity. For example, a TCR may be considered to have "antigenic specificity" for HPV 16 E6 if T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more) of interferon gamma (IFN-γ) upon co-culture with antigen-negative HLA-A2+ target cells pulsed with a low concentration of HPV 16 E6 peptide (e.g., about 0.05 ng/mL to about 5 ng/mL, 0.05 ng/mL, 0.1 ng/mL, 0.5 ng/mL, 1 ng/mL, or 5 ng/mL). Alternatively or additionally, a TCR may be considered to have "antigenic specificity" for HPV 16 E6 if T cells expressing the TCR secrete at least twice as much IFN-γ as the untransduced peripheral blood lymphocyte (PBL) background level of IFN-γ upon co-culture with antigen-negative HLA-A2+ target cells pulsed with a low concentration of HPV 16 E6 peptide. Cells expressing the inventive TCRs (including functional portions and functional variants thereof) may also secrete IFN-γ upon co-culture with antigen-negative HLA-A2+ target cells pulsed with higher concentrations of HPV 16 E6 peptide.

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for HPV 16 E6.

In an embodiment of the invention, the TCR comprises two polypeptide chains, each of which comprises a human variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and a second polypeptide chain comprising a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In this regard, the inventive TCR can comprise any one or more of the amino acid sequences selected from the group consisting of SEQ ID NOs: 3-8. Preferably, the TCR comprises the amino acid sequences of SEQ ID NOs: 3-5 or SEQ ID NOs: 6-8. In an especially preferred embodiment, the TCR comprises the amino acid sequences of SEQ ID NOs: 3-8.

In an embodiment of the invention, the TCR can comprise an amino acid sequence of a variable region of a TCR comprising the CDRs set forth above. In this regard, the TCR can comprise the amino acid sequence of SEQ ID NO: 9 (the variable region of an α chain), SEQ ID NO: 10 (the variable region of a β chain), or both SEQ ID NOs: 9 and 10. Preferably, the inventive TCR comprises the amino acid sequences of both SEQ ID NOs: 9 and 10.

The inventive TCRs may further comprise a constant region derived from any suitable species such as, e.g., human or mouse. In an embodiment of the invention, the inventive TCRs further comprise a murine constant region. In this regard, the TCR can comprise the amino acid sequence of SEQ ID NO: 15 (the constant region of a murine α chain), SEQ ID NO: 16 (the constant region of a murine β chain), or both SEQ ID NOs: 15 and 16. In a preferred embodiment, the inventive TCRs are chimeric TCRs comprising both a human variable region and a murine constant region.

In an embodiment of the invention, the inventive chimeric TCR may comprise a combination of a variable region and a constant region. In this regard, the TCR can comprise an alpha chain comprising the amino acid sequences of both of SEQ ID NO: 9 (the variable region of a human α chain) and SEQ ID NO: 15 (the constant region of a murine α chain), a beta chain comprising the amino acid sequence of both of SEQ ID NO: 10 (the variable region of a human β chain) and SEQ ID NO: 16 (the constant region of a murine β chain), or all of the amino acid sequences of SEQ ID NOs: 9-10 and 15-16.

As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively.

In an embodiment of the invention, the chimeric TCR can comprise an α chain of a TCR and a β chain of a TCR. Each of the α chain and β chain of the inventive chimeric TCR can independently comprise any amino acid sequence. Preferably, the α chain comprises the human variable region of an α chain and the murine constant region of an α chain as set forth above. In this regard, the inventive chimeric TCR can comprise the amino acid sequence of SEQ ID NO: 17. An α chain of this type can be paired with any β chain of a TCR. Preferably, the β chain of the inventive chimeric TCR comprises the human variable region of a β chain and the murine constant region of a β chain as set forth above. In this regard, the inventive chimeric TCR can comprise the amino acid sequence of SEQ ID NO: 18. The inventive chimeric TCR, therefore, can comprise the amino acid sequence of SEQ ID NO: 17, SEQ ID NO: 18, or both SEQ ID NOs: 17 and 18. Preferably, the inventive chimeric TCR comprises the amino acid sequences of both SEQ ID NOs: 17 and 18.

In an embodiment of the invention, the TCR is a human TCR. The human TCR may comprise any of the CDR regions as described herein with respect to other aspects of the invention. In this regard, an embodiment of the invention provides an isolated or purified TCR having antigenic specificity for HPV 16 E6 and comprising the amino acid sequences of SEQ ID NOs: 3-8. In another embodiment of the invention, the human TCR may comprise any of the variable regions described herein with respect to other aspects of the invention.

In an embodiment of the invention, the inventive human TCRs further comprise a human constant region. In this regard, the human TCR can comprise the amino acid sequence of SEQ ID NO: 13 (the constant region of a human α chain), SEQ ID NO: 14 (the constant region of a human β chain), or both SEQ ID NOs: 13 and 14.

In an embodiment of the invention, the inventive human TCR may comprise a combination of a variable region and a constant region. In this regard, the TCR can comprise an alpha chain comprising the amino acid sequences of both SEQ ID NO: 9 (the variable region of a human α chain) and SEQ ID NO: 13 (the constant region of a human α chain), a beta chain comprising the amino acid sequences of both SEQ ID NO: 10 (the variable region of a human β chain) and SEQ ID NO: 14 (the constant region of a human β chain), or all of the amino acid sequences of SEQ ID NOs: 9-10 and 13-14.

In an embodiment of the invention, the human TCR can comprise an α chain of a TCR and a β chain of a TCR. Each of the α chain and β chain of the inventive human TCR can independently comprise any amino acid sequence. Preferably, the α chain comprises the human variable region of an α chain and the human constant region of an α chain as set forth above. In this regard, the inventive human TCR can comprise the amino acid sequence of SEQ ID NO: 11. An α chain of this type can be paired with any β chain of a TCR. Preferably, the β chain of the inventive human TCR comprises the human variable region of a β chain and the human constant region of a β chain as set forth above. In this regard, the inventive human TCR can comprise the amino acid sequence of SEQ ID NO: 12. The inventive human TCR, therefore, can comprise the amino acid sequence of SEQ ID NO: 11, SEQ ID NO: 12, or both SEQ ID NOs: 11 and 12. Preferably, the inventive human TCR comprises the amino acid sequences of both SEQ ID NOs: 11 and 12.

Also provided by the invention is a polypeptide comprising a functional portion of any of the TCRs (or functional variants thereof) described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR (or functional variant thereof) of which it is a part, provided that the functional portion specifically binds to HPV 16 E6. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to HPV 16 E6 (e.g., in an HLA-A2-dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR (or functional variant thereof).

The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to HPV 16 E6; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or a combination thereof. Preferably, the inventive polypeptide comprises a functional portion comprising the amino acid sequences of SEQ ID NOs: 3-5; 6-8; or all of SEQ ID NOs: 3-8. More preferably, the polypeptide comprises a functional portion comprising the amino acid sequences of all of SEQ ID NOs: 3-8.

In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of SEQ ID NO: 9 (the variable region of an α chain), SEQ ID NO: 10 (the variable region of a β chain), or both SEQ ID NOs: 9 and 10. Preferably, the polypeptide comprises the amino acid sequences of both SEQ ID NOs: 9 and 10.

The inventive polypeptide may further comprise a constant region derived from any suitable species such as, e.g., human or mouse. In this regard, the polypeptide can comprise the amino acid sequence of SEQ ID NO: 13 (the constant region of a human α chain), SEQ ID NO: 14 (the constant region of a human β chain), SEQ ID NO: 15 (the constant region of a murine α chain), SEQ ID NO: 16 (the constant region of a murine β chain), both SEQ ID NOs: 13 and 14, or both SEQ ID NOs: 15 and 16. Preferably, the polypeptide comprises the amino acid sequences of both SEQ ID NOs: 13 and 14 or both SEQ ID NOs: 15 and 16.

In an embodiment of the invention, the inventive polypeptide may comprise a combination of a variable region and a constant region. In this regard, the polypeptide can comprise the amino acid sequences of both SEQ ID NOs: 9 and 15, both SEQ ID NOs: 9 and 13, both SEQ ID NOs: 10 and 16, both SEQ ID NOs: 10 and 14, all of SEQ ID NOs: 9-10 and 15-16, or all of SEQ ID NOs: 9-10 and 13-14.

In an embodiment of the invention, the inventive polypeptide can comprise the entire length of an α or β chain of one of the TCRs or functional variant thereof described herein. In this regard, the inventive polypeptide can comprise an amino acid sequence of SEQ ID NOs: 11, 12, 17, or 18. Alternatively, the polypeptide of the invention can comprise a and β chains of the TCRs or functional variants thereof described herein. For example, the inventive polypeptide can comprise the amino acid sequences of both SEQ ID NOs: 11 and 12 or both SEQ ID NOs: 17 and 18, both SEQ ID NOs: 11 and 18, or both SEQ ID NOs: 17 and 12. Preferably, the polypeptide comprises the amino acid sequences of both SEQ ID NOs: 11 and 12 or both SEQ ID NOs: 17 and 18.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5 and a second polypeptide chain comprising the amino acid sequence of SEQ ID NOs: 6-8. Alternatively or additionally, the protein of the invention can comprise a first polypeptide chain comprising the amino acid sequence of SEQ ID NO: 9, and a second polypeptide chain comprising the amino acid sequence of SEQ ID NO: 10. The protein of the invention can, for example, comprise a first polypeptide chain comprising the amino acid sequence of both SEQ ID NO: 9 and 13 or both SEQ ID NOs: 9 and 15, and a second polypeptide chain comprising the amino acid sequence of both SEQ ID NOs: 10 and 14 or both SEQ ID NOs: 10 and 16. The protein of the invention can, for example, comprise a first polypeptide chain comprising the amino acid sequence of SEQ ID NO: 11 or 17, and a second polypeptide chain comprising the amino acid sequence of SEQ ID NO: 12 or 18. In this instance, the protein of the invention can be a TCR. Alternatively, if, for example, the protein comprises a single polypeptide chain comprising the amino acid sequences of SEQ ID NO: 11 and 12 or SEQ ID NO: 17 and 18, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

In some embodiments of the invention, the TCRs (and functional portions and functional variants thereof), polypeptides, and proteins of the invention may be expressed as a single protein comprising a linker peptide linking the α chain and the β chain. In this regard, the TCRs (and functional variants and functional portions thereof), polypeptides, and proteins of the invention comprising the amino acid sequences of SEQ ID NO: 11 and 12 or SEQ ID NO: 17 and 18 may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. For example, the linker peptide may comprise the amino acid sequence of SEQ ID NO: 37. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)₂' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive TCRs described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to HPV 16 E6 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR (or functional variant thereof), polypeptide, or protein can consist essentially of the specified amino acid sequence or sequences described herein, such that other components of the TCR (or functional variant thereof), polypeptide, or protein, e.g., other amino acids, do not materially change the biological activity of the TCR (or functional variant thereof), polypeptide, or protein. In this regard, the inventive TCR (or functional variant thereof), polypeptide, or protein can, for example, consist essentially of the amino acid sequence of SEQ ID NO: 11, 12, 17, or 18, both SEQ ID NOs: 11 and 12, both SEQ ID NOs: 17 and 18, both SEQ ID NOs: 11 and 18, or both SEQ ID NOs: 17 and 12. Also, for instance, the inventive TCRs (including functional variants thereof), polypeptides, or proteins can consist essentially of the amino acid sequence(s) of SEQ ID NO: 9, 10, or both SEQ ID NOs: 9 and 10. Furthermore, the inventive TCRs (including functional variants thereof), polypeptides, or proteins can consist essentially of the amino acid sequence of SEQ ID NO: 3 (CDR1 of α chain), SEQ ID NO: 4 (CDR2 of α chain), SEQ ID NO: 5 (CDR3 of α chain), SEQ ID NO: 6 (CDR1 of β chain), SEQ ID NO: 7 (CDR2 of β chain), SEQ ID NO: 8 (CDR3 of β chain), or any combination thereof, e.g., SEQ ID NOs: 3-5; 6-8; or 3-8.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to HPV 16 E6; detect cancer, HPV 16 infection, or HPV-positive premalignancy in a mammal; or treat or prevent cancer, HPV 16 infection, or HPV-positive premalignancy in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional variants thereof) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention (including functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, N.Y. 2012; and Ausubel et al., *Current Protocols in Molecular Biology*, Greene Publishing Associates and John Wiley & Sons, N Y, 1994. Further, some of the TCRs, polypeptides, and proteins of the invention (including functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs (including functional variants thereof), polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention provides a nucleic acid comprising a nucleotide sequence that encodes any of the TCRs, polypeptides, and proteins herein. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, proteins, or functional functional variants thereof described herein. In an embodiment of the invention, the nucleotide sequence may comprise, consist, or consist essentially of all of SEQ ID NOs: 31-36 (encoding CDR1α, CDR2α, CDR3α, CDR1β, CDR2β, CDR3β, respectively); all of SEQ ID NOs: 31-33; all of SEQ ID NOs: 34-36; both of SEQ ID NOs: 19-20 (encoding variable regions of α and β chains, respectively); both of SEQ ID NOs: 23-24 (encoding human constant region of α and β chains, respectively); both of SEQ ID NOs: 25-26 (encoding murine constant region of α and β chains, respectively), all of SEQ ID NOs: 19-20 and 23-24, all of SEQ ID NOs: 19-20 and 25-26, both of SEQ ID NOs: 21-22 (encoding human α and β chains, respectively), or both of SEQ ID NOs: 27-28 (encoding chimeric α and β chains, respectively). In another embodiment of the invention, the nucleotide sequence may comprise, consist, or consist essentially of any one of SEQ ID NOs: 19-28 and 31-36.

In an embodiment of the invention, the nucleic acid comprises a non-natural nucleotide sequence. A nucleotide sequence may be considered to be "non-natural" if the nucleotide sequence is not found in nature. In some embodiments, the nucleotide sequence may be codon-optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In an embodiment of the invention, the codon-optimized nucleotide sequence may comprise, consist, or consist essentially of SEQ ID NO: 38 (variable region of α chain), SEQ ID NO: 39 (variable region of β chain), or SEQ ID NOs: 38 and 39.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs (including functional portions and functional variants thereof). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. In an embodiment of the invention, the recombinant expression vector comprises a nucleotide sequence encoding the α chain, the β chain, and linker peptide. For example, in an embodiment, the recombinant expression vector comprises a codon-optimized nucleotide sequence comprising SEQ ID NO: 29 (encoding chimeric α and β chains SEQ ID NOs: 17 and 18 with a linker positioned between them).

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is a viral vector, e.g., a retroviral vector. In an especially preferred embodiment, the recombinant expression vector is an MSGV1 vector. In an embodiment, an MSGV1 vector comprising a codon-optimized nucleotide sequence encoding a chimeric TCR comprising SEQ ID NOs: 17 and 18 of the invention comprises the nucleotide sequence of SEQ ID NO: 30.

The recombinant expression vectors of the invention can be prepared using standard recombinant DNA techniques described in, for example, Green and Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional variants thereof), or to the nucleotide sequence which is complementary to or which hybridizes to the nucleotide sequence encoding the TCR, polypeptide, or protein (including functional variants thereof). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5a cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+$/ $CD8^+$ double positive T cells, $CD4^+$ helper T cells, e.g., $Th_1$ and $Th_2$ cells, CD4+ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990).

The invention further provides an antibody, or antigen binding portion thereof, which specifically binds to a functional portion of any of the TCRs (or functional variant thereof) described herein. Preferably, the functional portion specifically binds to the cancer antigen, e.g., the functional portion comprising the amino acid sequence SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), SEQ ID NO: 9 (variable region of α chain), SEQ ID NO: 10 (variable region of β chain), or a combination thereof, e.g., 3-5; 6-8; 3-8; 9; 10; or 9-10. More preferably, the functional portion comprises the amino acid sequences of SEQ ID NOs: 3-8 or SEQ ID NOs: 9 and 10. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR (or functional variant thereof). Desirably, the antibody is specific for the functional portion of the inventive TCR (or functional variants thereof), such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 8$^{th}$ Ed., Garland Publishing, New York, N.Y. (2011)). Alternatively, other methods, such as EBV-hybridoma methods (Haskard and Archer, *J. Immunol. Methods,* 74(2), 361-67 (1984), and Roder et al., *Methods Enzymol.*, 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate the antibody of the invention. In this regard, phage libraries encoding antigen-binding variable (V) domains of antibodies can be generated using standard molecular biology and recombinant DNA techniques (see, e.g., Green and Sambrook et al. (eds.), *Molecular Cloning, A Laboratory Manual,* 4$^{th}$ Edition, Cold Spring Harbor Laboratory Press, New York (2012)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in, for example, U.S. Pat. No. 5,639,641 and Pedersen et al., *J. Mol. Biol.,* 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering,* 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public.

It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR (or functional variant or functional portion thereof), polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. In an embodiment in which the inventive TCR material is a population of cells, the number of cells administered per infusion may vary, e.g., from about $1 \times 10^6$ to about $1 \times 10^{12}$ cells or more.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to HPV 16 E6; or to detect, treat, or prevent cancer, HPV 16 infection, or HPV-positive premalignancy.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer, HPV 16 infection, or HPV-positive premalignancy. Without being bound to a particular theory, the inventive TCRs (and functional variants thereof) are believed to bind specifically to HPV 16 E6, such that the TCR (or related inventive polypeptide or protein and functional variants thereof), when expressed by a cell, is able to mediate an immune response against a target cell expressing HPV 16 E6. In this regard, the invention provides a method of treating or preventing a condition in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent the condition in the mammal, wherein the condition is cancer, HPV 16 infection, or HPV-positive premalignancy.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, HPV 16 infection, or HPV-positive premalignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer of the uterine cervix, oropharynx, anus, anal canal, anorectum, vagina, vulva, or penis. A particularly preferred cancer is HPV 16-positive cancer. While the cancers most commonly associated with HPV 16 infection include cancer of the uterine cervix, oropharynx, anus, anal canal, anorectum, vagina, vulva, and penis, the inventive methods may be used to treat any HPV 16-positive cancer, including those that occur at other anatomical areas.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of human anti-HPV 16 TCRs from tumor.

A sample of a metastatic HPV 16 E6-positive anal cancer tumor (tumor 3809) was obtained from a patient. The tumor sample was analyzed for expression of HPV 16 E6, HPV 16 E7, HPV 18 E6, and HPV 18 E7 relative to glyceraldehyde 3-phosphate dehydrogenase (GAPDH) by reverse transcriptase (RT) polymerase chain reaction (PCR). Relative expression of HPV 16 E6, HPV 16 E7, HPV 18 E6, and HPV 18 E7 was compared to that of CaSki cells, HeLa cells, and 624 cells (melanoma cell line). The results are shown in FIG. 1. As shown in FIG. 1, the tumor 3809 sample was positive for HPV 16 E6 expression.

Figure 2A:
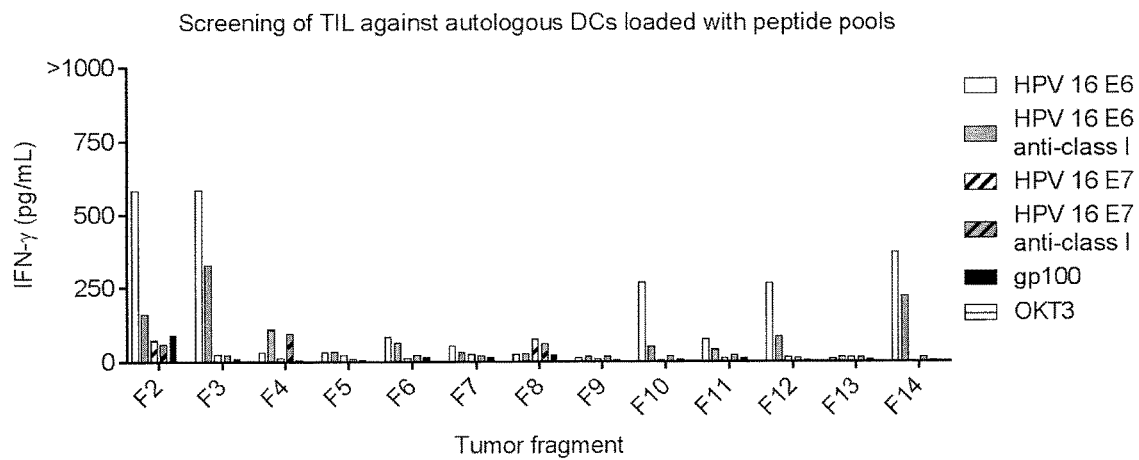
FIGS. 2A and 2B are bar graphs showing interferon-gamma (IFN-γ) (pg/mL) secreted by tumor infiltrating lymphocytes (TIL) from fragments (F) 2-14 of tumor 3809 (A), fragments 15-24 (B) of tumor 3809, or melanoma TIL upon co-culture with autologous dendritic cells (DCs) which had been pulsed with HPV 16 E6 alone (white bars), HPV 16 E6 in combination with anti-class I antibody (shaded unhatched bars), HPV 16 E7 alone (unshaded hatched bars), HPV 16 E7 in combination with anti-class I antibody (shaded hatched bars), gp100 (black bars), or OKT3 (horizontal striped bars).
Figure 2B:
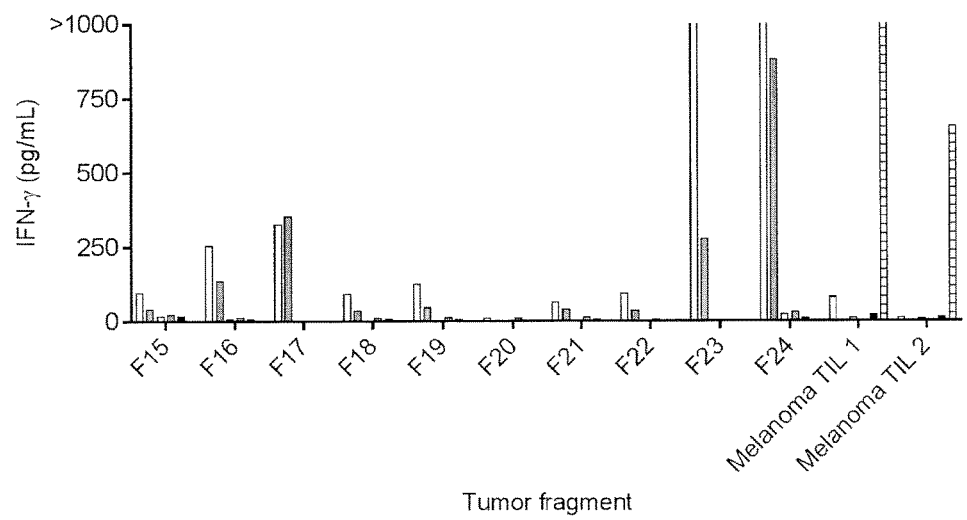

The tumor 3809 sample was divided into 24 fragments and tumor infiltrating lymphocytes (TIL) were obtained from the various fragments. The TIL were co-cultured in a 96-well plate with autologous immature dendritic cells (DCs) which had been pulsed with HPV 16 E6 alone, HPV 16 E6 in combination with anti-class I antibody, HPV 16 E7 alone, HPV 16 E7 in combination with anti-class I antibody, gp100, or OKT3. Interferon-gamma (IFN-γ) was measured. The results are shown in FIGS. 2A and 2B. As shown in FIGS. 2A and 2B, TIL were reactive against HPV 16 E6 but not gp100 or E7. The anti-HPV 16 E6 reactivity of the TIL was blocked by anti-class I antibody.

Cells from the reactive co-culture wells were selected using anti-4-1BB magnetic beads. Rapid expansion of the numbers of selected cells was performed using the Rapid Expansion Protocol (REP) as previously described (Dudley et al. *J. Immunother.* 26:332-42 (2003) and Riddell et al. *J. Immunol. Methods* 128:189-201 (1990)). Briefly, TIL were cultured with irradiated (40 Gy) allogeneic peripheral blood mononuclear "feeder" cells in complete medium (CM) with 30 ng/mL anti-CD3 antibody and 6000 IU/mL IL-2.

Figure 3:
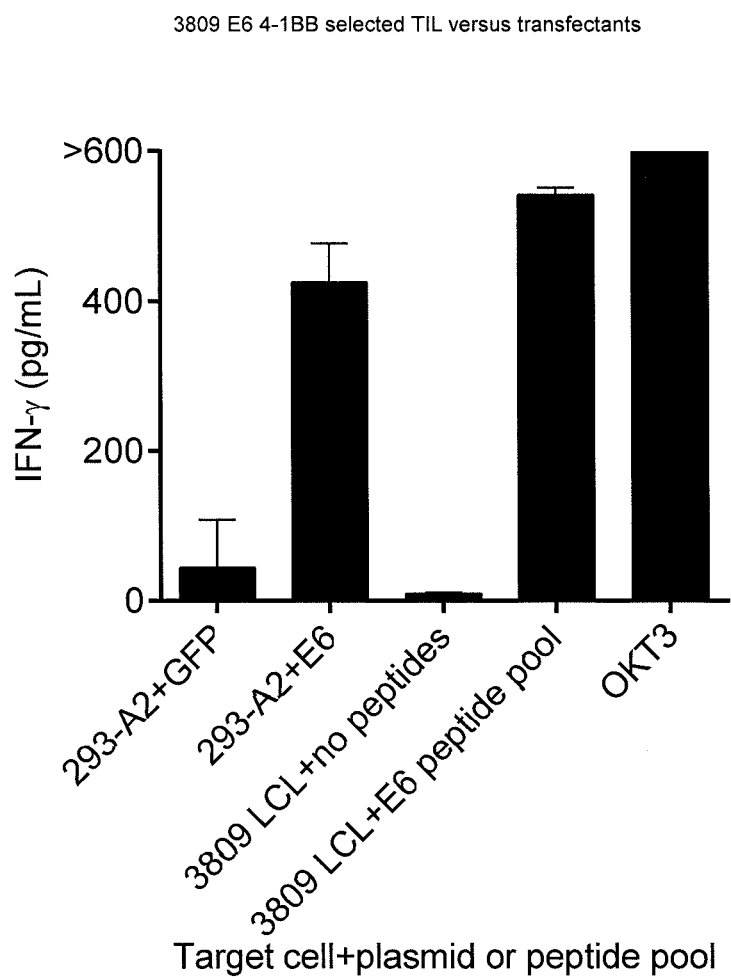
FIG. 3 is a bar graph showing IFN-γ (pg/mL) secreted by expanded numbers of 3809 4-1BB-selected TIL upon co-culture with 293-A2 cells (HEK-293 cells with stable expression of HLA-A2) transfected with green fluorescent protein (GFP), 293-A2 cells transfected with HPV 16 E6, 3809 lymphoblastoid cell line (LCL) (B cells that have been transformed using Epstein-Barr virus) cultured without peptide, 3809 LCL co-cultured with an HPV 16 E6 peptide pool, or OKT3.

The expanded numbers of 3809 4-1BB-selected cells were co-cultured with 293-A2 cells (HEK-293 cells with stable expression of HLA-A2) transfected with green fluorescent protein (GFP), 293-A2 cells transfected with E6, 3809 lymphoblastoid cell line (LCL) (B cells that have been transformed using Epstein-Barr virus) cultured without peptide, 3809 LCL co-cultured with an HPV 16 E6 peptide pool, or OKT3. The peptide pool included 15-mer peptides with 11-amino-acid overlaps that covered the complete sequence of HPV 16 E6. IFN-γ was measured. The results are shown in FIG. 3. As shown in FIG. 3, the expanded numbers of TIL were reactive against 293-A2 cells transfected with E6 but not 293-A2 cells transfected with GFP. The 3809 LCL cells co-cultured with the E6 peptide pool demonstrated reactivity while the 3809 LCL cells co-cultured with no peptides did not. Flow cytometry studies showed that the expanded numbers of cells bound to HLA-A2/E6$_{29-38}$ tetramer.

Cells were further selected by sorting using anti-4-1BB magnetic beads without further cycles of REP or cloning followed by 5' Rapid Amplification of cDNA Ends (RACE). A genotype analysis of the 5' RACE products from the magnetic bead isolation is shown in Table A. As shown in Table A, a nearly clonal population of cells was obtained.

TABLE A

| TRAV | TRAJ | Colonies | TRBV | TRBJ | TRBD | Colonies |
|---|---|---|---|---|---|---|
| TRAV35*02 | TRAJ41*01 | 4 | TRBV7-6*01 | TRBV2-3*01 | TRBD1*01 | 8 |
| TRAV10*01 | TRAJ44*01 | 3 | TRBV14*01 | TRBJ1-6*01 | TRBD1*01 | 1 |
| TRAV5*01 | TRAJ34*01 | 1 | | | | |

A nucleotide sequence comprising cDNA (SEQ ID NO: 21) encoding an alpha chain comprising the amino acid sequence of SEQ ID NO: 11 was obtained from TRAV35*02/TRAJ41*01. A nucleotide sequence comprising cDNA (SEQ ID NO: 22) encoding a beta chain comprising the amino acid sequence of SEQ ID NO: 12 was obtained from TRBV7-6*01/TRBV2-3*01/TRBD1*01.

Example 2

This example demonstrates a method of making a chimeric anti-HPV 16 TCR comprising a human variable region and a mouse constant region.

A nucleotide sequence encoding a chimeric TCR including a mouse constant region and a human variable region was prepared as follows. The nucleotide sequences encoding the original (human) constant regions of the alpha and beta chains of the TCR obtained in Example 1 (constant region amino acid sequences of SEQ ID NOs: 23 and 24, respectively) were excised and replaced with nucleotide sequences encoding a murine constant region of the alpha and beta chains, respectively. The resulting nucleotide sequences encoding the chimeric alpha and beta chains were cloned into a single nucleotide sequence with a nucleotide sequence encoding a picornavirus 2A peptide positioned between the alpha and beta chains. The combined nucleotide sequence was codon-optimized (opt) for expression in human tissues to provide a vector insert (SEQ ID NO: 29). The vector insert was cloned into an MSGV1 expression vector resulting in the nucleotide sequence of SEQ ID NO: 30 (E6 TCR). The TCR encoded by the vector comprised an alpha chain comprising an amino acid sequence comprising SEQ ID NO: 17 and a beta chain comprising an amino acid sequence comprising SEQ ID NO: 18.

Example 3

This example demonstrates that peripheral blood lymphocytes (PBL) transduced with a recombinant expression vector encoding the amino acid sequences of SEQ ID NOs: 17 and 18 specifically recognize HPV 16-positive tumor cell lines in an HLA-A2-restricted manner.

Figure 4A:
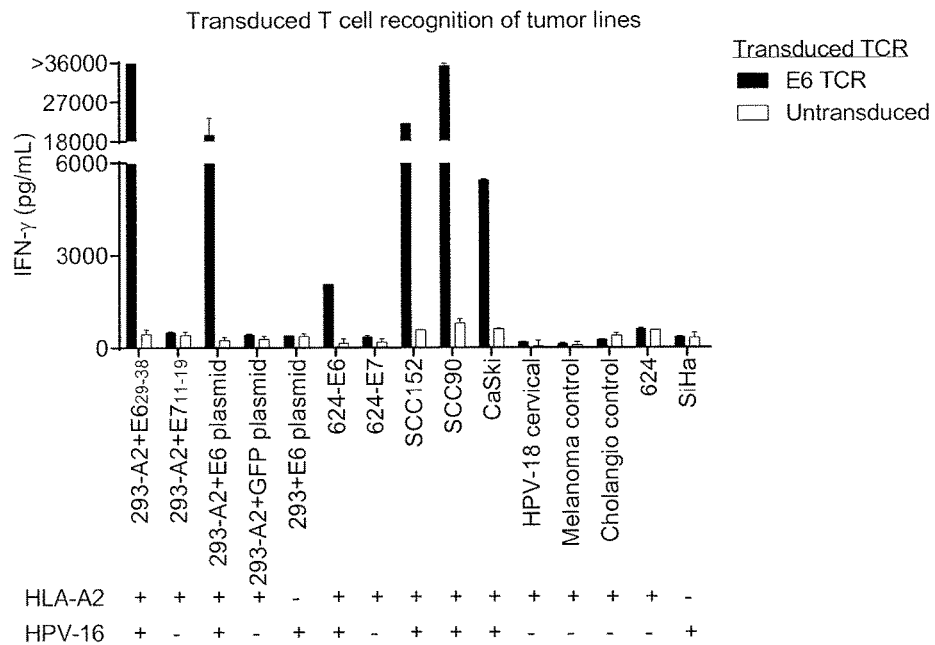
FIG. 4A is a bar graph showing IFN-γ (pg/mL) secreted by peripheral blood lymphocytes (PBL) that were not transduced (untransduced) (unshaded bars) or transduced with a nucleotide sequence encoding SEQ ID NOs: 17 and 18 (E6 TCR; shaded bars) upon co-culture with target 293-A2 cells pulsed with HPV 16 E6$_{29-38}$ peptide, 293-A2 cells pulsed with HPV 16 E7$_{11-19}$ peptide, 293-A2 cells transduced with a plasmid encoding HPV 16 E6, 293-A2 cells transduced with a plasmid encoding GFP, 293 cells transduced with a plasmid encoding HPV 16 E6, 624 cells transduced with a plasmid encoding HPV 16 E6, 624 cells transduced with a plasmid encoding HPV 16 E7, SCC152 cells, SCC90 cells, CaSki cells, HPV-18 cervical cancer cells, melanoma control cells, cholangio control cells, 624 cells, or SiHa cells. HLA-A2 and HPV-16 expression by each target cell is indicated in the bottom of FIG. 4A ("+" indicates positive for expression and "−" indicates negative for expression).

Peripheral blood lymphocytes (PBL) were transduced with the expression vector of Example 2 and were co-cultured with target 293-A2 cells pulsed with HPV 16 E6$_{29-38}$ peptide, 293-A2 cells pulsed with HPV 16 E7$_{11-19}$ peptide, 293-A2 cells transduced with a plasmid encoding HPV 16 E6, 293-A2 cells transduced with a plasmid encoding GFP, 293 cells transduced with a plasmid encoding HPV 16 E6, 624 cells transduced with a plasmid encoding HPV 16 E7, SCC152 cells, SCC90 cells, CaSki cells, HPV-18 cervical cancer cells, melanoma control cells, cholangio control cells, 624 cells, or SiHa cells. IFN-γ was measured. The results are shown in FIG. 4A. As shown in FIG. 4A, PBMC transduced with a recombinant expression vector encoding the amino acid sequences of SEQ ID NOs: 17 and 18 specifically recognizes HPV 16-positive tumor cell lines and other HLA-A2$^+$HPV16$^+$ targets in an HLA-A2-restricted manner.

Figure 4B:
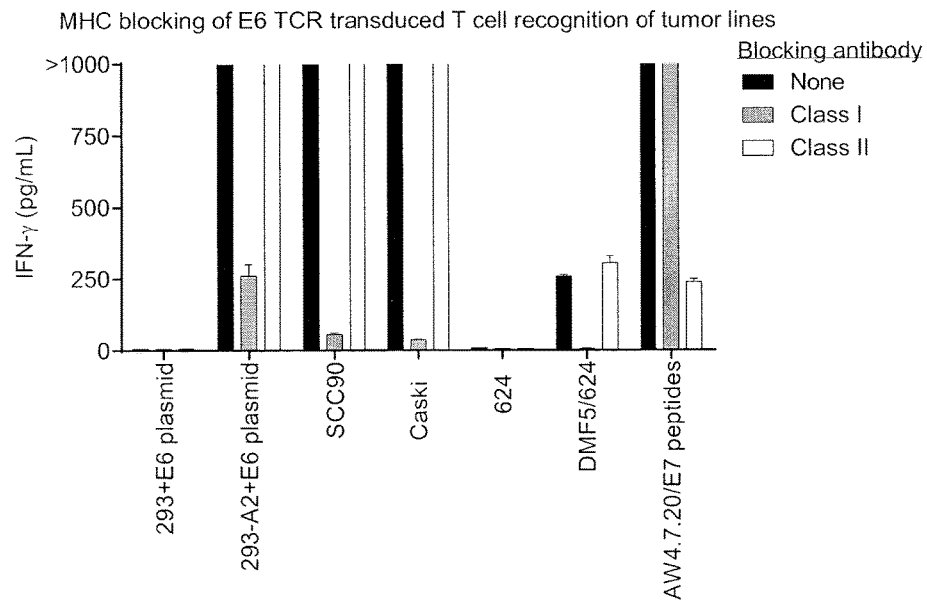
FIG. 4B is a bar graph showing IFN-γ (pg/mL) secreted by PBL transduced with a nucleotide sequence encoding SEQ ID NOs: 17 and 18 upon co-culture with target 293-A2 cells transduced with a plasmid encoding HPV 16 E6, 293 cells transduced with a plasmid encoding HPV 16 E6, SCC90 cells, CaSki cells, 624 cells, DMF/624 cells, or 4.7.20 cells pulsed with HPV 16 E7 peptides with no antibody (black bars), anti-MHC Class I antibody (grey bars), or anti-MHC Class II antibody (unshaded bars).

PBL transduced with the expression vector of Example 2 were co-cultured with target 293-A2 cells transduced with a plasmid encoding E6, 293 cells transduced with a plasmid encoding E6, SCC90 cells, CaSki cells, or 624 cells (melanoma cell line) with no antibody, anti-MHC Class I antibody, or anti-MHC Class II antibody. DMF5 (T cells transduced to express a MHC class I-restricted TCR against MART-1) were co-cultured with a melanoma cell line (624) that is recognized by DMF5 with no antibody, anti-MHC Class I antibody, or anti-MHC Class II antibody. 4.7.20 (T cells transduced to express a MHC class II-restricted TCR against HPV 16 E7) were cultured with PBMC pulsed with the E7 peptide pool "E7 peptides" with no antibody, anti-MHC Class I antibody, or anti-MHC Class II antibody. IFN-γ was measured. The results are shown in FIG. 4B. As shown in FIG. 4B, anti-MHC Class I antibody blocked the reactivity of the transduced cells against HLA-A2$^+$HPV16$^+$ targets, while anti-Class II antibody did not block reactivity.

Example 4

This example demonstrates that cells transduced with a recombinant expression vector encoding the amino acid sequences of SEQ ID NOs: 17 and 18 bind to HLA-A2-E6$_{29-38}$ tetramer in a CD8-independent manner.

PBL transduced with the recombinant expression vector of Example 2 was sorted into CD8-positive cells and CD8-negative cells by FACS. Binding to HLA-A2-E6$_{29-38}$ tetramer was measured by flow cytometry. CD8-positive and CD8-negative cells both bound to HLA-A2-E6$_{29-38}$ tetramer.

Example 5

This example demonstrates that CD4 and CD8-positive cells transduced with a recombinant expression vector encoding the amino acid sequences of SEQ ID NOs: 17 and 18 specifically recognize HPV-16 positive tumor cell lines.

Figure 5:
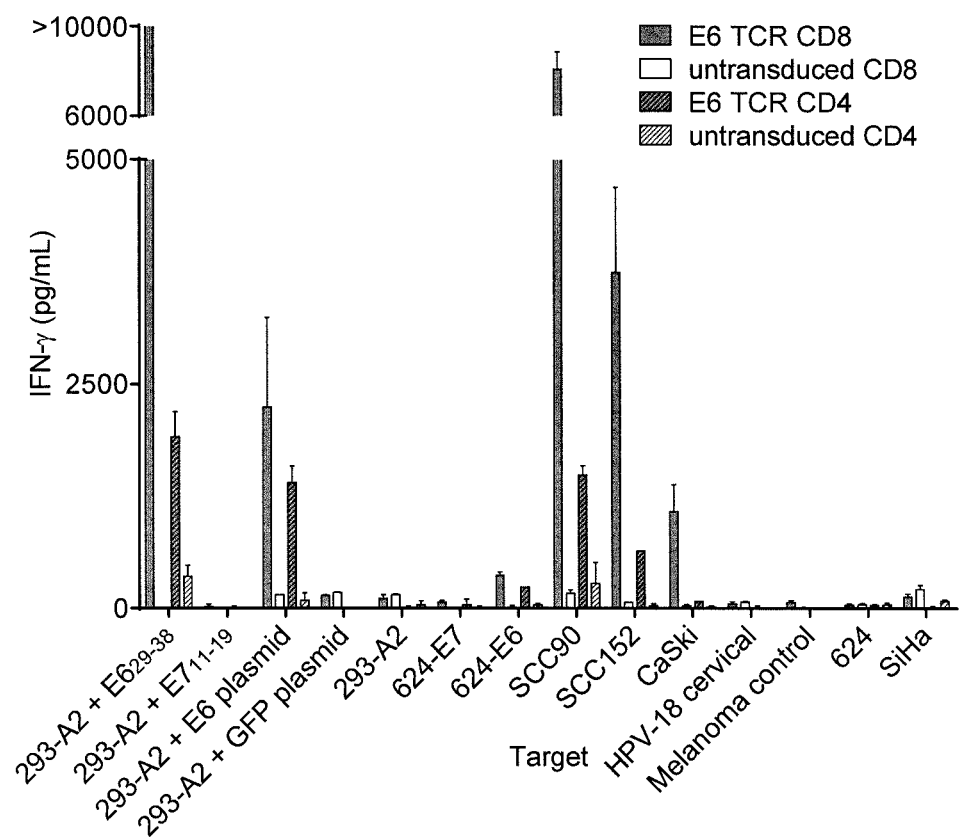
FIG. 5 is a bar graph showing IFN-γ (pg/mL) secreted by untransduced CD8-positive PBL (unshaded unhatched bars), untransduced CD4-positive PBL (cross-hatched unshaded bars), or PBL (CD8 positive (E6 TCR; shaded unhatched bars) or CD4 positive (E6 TCR; cross-hatched shaded bars)) that were transduced with a nucleotide sequence encoding SEQ ID NOs: 17 and 18 upon co-culture with target 293-A2 cells pulsed with HPV 16 $E6_{29-38}$ peptide, 293-A2 cells pulsed with HPV 16 $E7_{11-19}$ peptide, 293-A2 cells transduced with a plasmid encoding HPV 16 E6, 293-A2 cells transduced with a plasmid encoding GFP, 293-A2 cells, 624 cells transduced with a plasmid encoding HPV 16 E7, 624 cells transduced with a plasmid encoding HPV 16 E6, SCC152 cells, SCC90 cells, CaSki cells, HPV-cervical cancer cells, melanoma control cells, 624 cells, or SiHa cells.

CD8-positive or CD4-positive PBL were not transduced (untransduced) or transduced with the expression vector of Example 2 and were co-cultured with target 293-A2 cells pulsed with HPV 16 E6$_{29-38}$ peptide, 293-A2 cells pulsed with HPV 16 E7$_{11-19}$ peptide, 293-A2 cells transduced with a plasmid encoding HPV 16 E6, 293-A2 cells transduced with a plasmid encoding GFP, 293-A2 cells, retrovirus-transduced 624 cells stably expressing HPV 16 E7 (624-E7), retrovirus-transduced 624 cells stably expressing HPV 16 E6 (624-E6), SCC152 cells, SCC90 cells, CaSki cells, HPV-18 cervical cancer cells, melanoma control cells, 624 cells, or SiHa cells. IFN-γ was measured. The results are shown in FIG. 5. As shown in FIG. 5, CD8 positive and CD4 positive PBMC transduced with a recombinant expression vector encoding the amino acid sequences of SEQ ID NOs: 17 and 18 both specifically recognize HPV 16-positive tumor cell lines and other HLA-A2$^+$HPV16$^+$ targets in an HLA-A2-restricted manner.

Example 6

This example demonstrates that cells transduced with a recombinant expression vector encoding the amino acid sequences of SEQ ID NOs: 17 and 18 demonstrate avid recognition of HPV 16 E6$_{29-38}$-pulsed T2 cells.

Figure 6A:
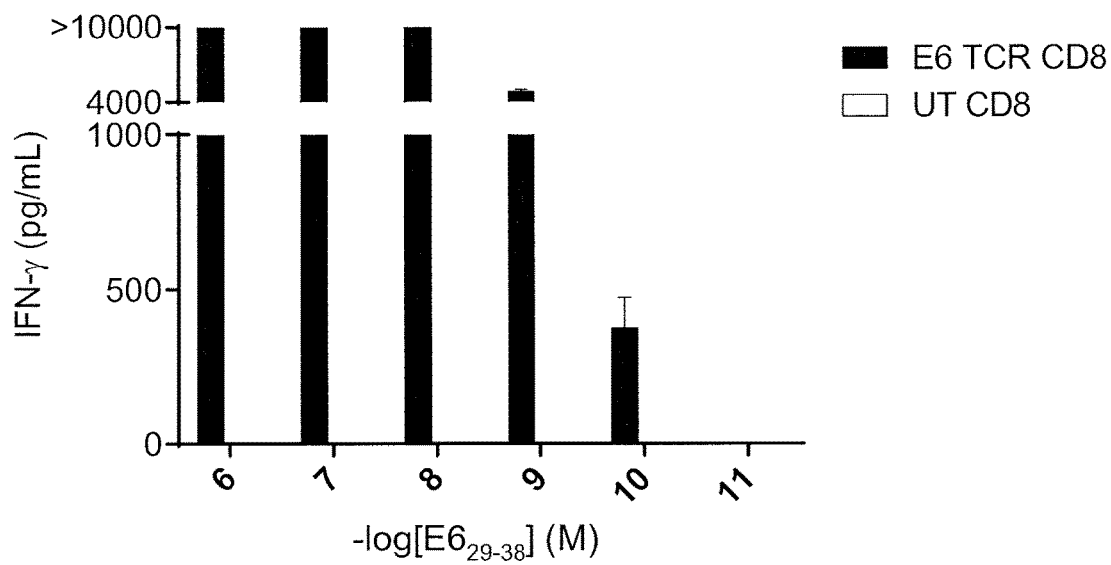
FIG. 6A is a bar graph showing IFN-γ (pg/mL) secreted by untransduced (UT) CD8-positive PBL (unshaded bars) or CD8 positive PBL transduced with a nucleotide sequence encoding SEQ ID NOs: 17 and 18 (shaded bars) upon co-culture with target T2 cells pulsed with varying concentrations of $E6_{29-38}$ peptide (−log M).
Figure 6B:
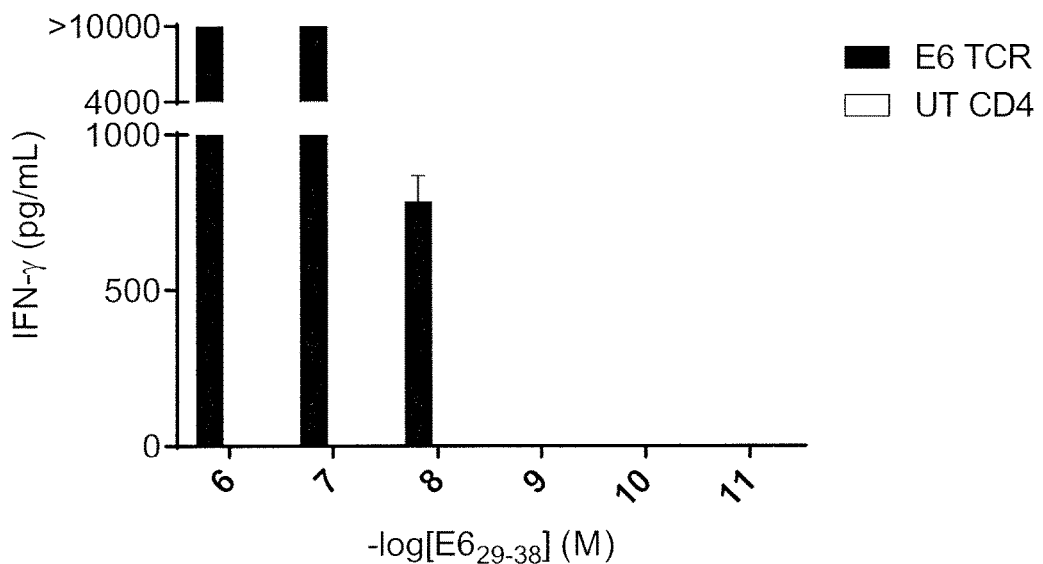
FIG. 6B is a bar graph showing IFN-γ (pg/mL) secreted by untransduced CD4-positive PBL (unshaded bars) or CD4 positive PBL transduced with a nucleotide sequence encoding SEQ ID NOs: 17 and 18 (E6 TCR; shaded bars) upon co-culture with target T2 cells pulsed with varying concentrations of $E6_{29-38}$ peptide (−log M).

CD8-positive or CD4-positive PBL were not transduced (untransduced) or transduced with the expression vector of Example 2 and were co-cultured with target T2 cells pulsed with varying concentrations of HPV 16 E6$_{29-38}$ peptide. IFN-γ was measured. The results are shown in FIGS. 6A and 6B. As shown in FIGS. 6A and 6B, CD4 positive and CD8 positive cells transduced with a recombinant expression vector encoding the amino acid sequences of SEQ ID NOs: 17 and 18 demonstrated avid recognition of HPV 16 E6$_{29-38}$-pulsed T2 cells.

Example 7

This example demonstrates a method of treating HPV 16$^+$ cancer in a human patient, comprising administering to the patient autologous T cells transduced to express an anti-HPV 16 E6$_{29-38}$ TCR comprising the amino acid sequences of SEQ ID NOs: 17 and 18.

Patients will have recurrent/refractory or metastatic HPV-16$^+$ cancer. A sample of cancerous tissue will be tested for HPV 16 genotype by in situ hybridization (ISH) or PCR. Patients will also be tested for HLA-A2 expression. The patients will have had a prior first line treatment for recurrent/refractory or metastatic disease, or the patient will have declined standard therapy.

Patients will be treated with cyclophosphamide (60 mg/kg/day intravenously (IV)) on days −7 and −6 and fludarabine (25 mg/m2/day IV) on days −5 through −1. Autologous PBMC will be transduced with the MSGV1 expression vector of Example 2. The numbers of transduced cells will be rapidly expanded as previously described (Dudley et al. *J. Immunother.* 26:332-42 (2003) and Riddell et al. *J. Immunol. Methods* 128:189-201 (1990)). Briefly, cells will be cultured with irradiated (40 Gy) allogeneic peripheral blood mononuclear "feeder" cells in complete medium (CM) with 30 ng/mL anti-CD3 antibody and 6000 IU/mL IL-2. Expanded numbers of transduced cells will be administered to the patients along with a high dose of interleukin (IL)-2 on day 0.

Objective tumor responses will be evaluated according to RECIST (Response Evaluation Criteria In Solid Tumors) 1.0. If at least three out of 18 patients respond to treatment at four months or more after treatment, the cohort will be expanded to 35 patients. Toxicity will also be evaluated. Immunological studies (including, for example, expansion, persistence, phenotype, and function of the infused cells) will also be studied.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a polypeptide comprising the alpha chain CDR1 amino acid sequence of SEQ ID NO: 3, the alpha chain CDR2 amino acid sequence of SEQ ID NO: 4, the alpha chain CDR3 amino acid sequence of SEQ ID NO: 5, the beta chain CDR1 amino acid sequence of SEQ ID NO: 6, the beta chain CDR2 amino acid sequence of SEQ ID NO: 7, and the beta chain CDR3 amino acid sequence of SEQ ID NO: 8.

2. The nucleic acid according to claim 1, wherein the nucleotide sequence is codon-optimized.

3. A recombinant expression vector comprising the nucleic acid according to claim 1.

4. An isolated host cell comprising the recombinant expression vector of claim 3.

5. The host cell according to claim 4, wherein the cell is human.

6. A population of cells comprising at least one host cell of claim 4.

7. A pharmaceutical composition comprising the population of cells of claim 6 and a pharmaceutically acceptable carrier.

8. A method of detecting the presence of a condition in a mammal, comprising:
   (a) contacting a sample comprising one or more cells from the mammal with the host cell of claim 4, thereby forming a complex, and (b) detecting the complex, wherein detection of the complex is indicative of the presence of the condition in the mammal, wherein the condition is cancer, HPV 16 infection, or HPV-positive premalignancy.

9. The method of claim 8, wherein the condition is cancer of the uterine cervix, oropharynx, anus, anal canal, anorectum, vagina, vulva, or penis.

10. The method of claim 8, wherein the condition is an HPV 16-positive cancer.

11. A method of treating or preventing a condition in a mammal, comprising administering the population of cells of claim 6 to the mammal in an amount effective to treat or prevent the condition in the mammal, wherein the condition is cancer, HPV 16 infection, or HPV-positive premalignancy.

12. The method of claim 11, wherein the condition is cancer of the uterine cervix, oropharynx, anus, anal canal, anorectum, vagina, vulva, or penis.

13. The method of claim 11, wherein the condition is an HPV 16-positive cancer.

14. The isolated or purified nucleic acid of claim 1, wherein the polypeptide comprises the amino acid sequences of (a) SEQ ID NO: 9, (b) SEQ ID NO: 10, or (c) SEQ ID NOs: 9 and 10.

15. The isolated or purified nucleic acid of claim 1, wherein the polypeptide comprises the amino acid sequence (s) of (a) SEQ ID NO: 11, (b) SEQ ID NO: 12, or (c) SEQ ID NOs: 11 and 12.

16. The isolated or purified nucleic acid of claim 1, wherein the polypeptide comprises the amino acid sequence (s) of (a) SEQ ID NO: 17, (b) SEQ ID NO: 18, or (c) SEQ ID NOs: 17 and 18.

17. A recombinant expression vector comprising the nucleic acid according to claim 14.

18. A recombinant expression vector comprising the nucleic acid according to claim 15.

19. A recombinant expression vector comprising the nucleic acid according to claim 16.

20. A population of cells comprising at least one host cell comprising the recombinant expression vector of claim 17.

* * * * *